(12) United States Patent
Reiner et al.

(10) Patent No.: US 10,351,521 B2
(45) Date of Patent: *Jul. 16, 2019

(54) ALKYLAROMATIC SULFONATE COMPOSITIONS FROM MIXED HYDROCARBONS

(71) Applicant: ExxonMobil Chemical Patents Inc., Baytown, TX (US)

(72) Inventors: Virginia M. Reiner, Summit, NJ (US); Jingwen Zhang, Houston, TX (US); Tracie L. Owens, Houston, TX (US); Mosha H. Zhao, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 37 days.

This patent is subject to a terminal disclaimer.

(21) Appl. No.: 15/672,948

(22) Filed: Aug. 9, 2017

(65) Prior Publication Data

US 2018/0057453 A1    Mar. 1, 2018

Related U.S. Application Data

(60) Provisional application No. 62/382,343, filed on Sep. 1, 2016.

(51) Int. Cl.
*C07C 7/04* (2006.01)
*C07C 7/10* (2006.01)
(Continued)

(52) U.S. Cl.
CPC .............. *C07C 309/31* (2013.01); *C07C 7/04* (2013.01); *C07C 7/10* (2013.01); *C07C 15/107* (2013.01);
(Continued)

(58) Field of Classification Search
None
See application file for complete search history.

(56) References Cited

U.S. PATENT DOCUMENTS

| 2,531,324 A | 11/1950 | Cope et al. |
| 3,351,672 A | 11/1967 | Adams et al. |
| (Continued) | | |

FOREIGN PATENT DOCUMENTS

| CN | 1203935 | 1/1999 |
| CN | 1205387 | 1/1999 |
| (Continued) | | |

OTHER PUBLICATIONS

Griess, Fette-Seifen-Anstrichmittel, 1955, vol. 57, No. 1, pp. 24-32.
(Continued)

*Primary Examiner* — Tam M Nguyen

(57) ABSTRACT

Provided herein are various methods for forming alkylaromatic sulfonate compositions and blended alkylaromatic sulfonate compositions, and such compositions themselves. The methods of various embodiments include obtaining a $C_8$-$C_{30}$ hydrocarbon mixture, optionally treating the mixture to concentrate the mixture in sulfonatable aromatics, and sulfonating the mixture to form the alkylaromatic sulfonates. The mixture or treated mixture may be blended with linear alkyl benzene (LAB) compositions and sulfonated, and/or the alkylaryl sulfonates may be blended with linear alkylbenzene sulfonate (LAS) compositions, to form the blended alkylaromatic sulfonates of some embodiments. These compositions and processes for making them may be tailored to serve a variety of end uses, such as detergents in cleaning solutions or for enhanced oil recovery operations, and/or as low foaming and/or hydrotropic additives in detergent formulations, and the like.

10 Claims, 9 Drawing Sheets

(51) Int. Cl.

| | | |
|---|---|---|
| *C07C 309/31* | (2006.01) | |
| *C07C 309/37* | (2006.01) | |
| *C07C 303/06* | (2006.01) | |
| *C07C 15/107* | (2006.01) | |
| *G01N 13/02* | (2006.01) | |
| *E21B 43/16* | (2006.01) | |
| *C09K 8/584* | (2006.01) | |

(52) U.S. Cl.
CPC .......... *C07C 303/06* (2013.01); *C07C 309/37* (2013.01); *C09K 8/584* (2013.01); *E21B 43/16* (2013.01); *G01N 13/02* (2013.01); *G01N 2013/0275* (2013.01); *G01N 2013/0283* (2013.01)

(56) References Cited

U.S. PATENT DOCUMENTS

| | | | |
|---|---|---|---|
| 3,591,498 | A | 7/1971 | Benbury et al. |
| 3,798,261 | A | 3/1974 | Kemp |
| 3,954,677 | A * | 5/1976 | Law .................... B01F 17/0057 516/77 |
| 3,970,690 | A | 7/1976 | Suzuki et al. |
| 4,013,549 | A | 3/1977 | Bushnell |
| 4,177,207 | A | 12/1979 | Nussbaum et al. |
| 4,252,192 | A | 2/1981 | Nussbaum et al. |
| 4,560,517 | A | 12/1985 | Schroeder, Jr. et al. |
| 4,614,623 | A | 9/1986 | Schroeder, Jr. et al. |
| 4,692,270 | A | 9/1987 | Sato et al. |
| 4,909,927 | A | 3/1990 | Bell |
| 6,432,884 | B1 | 8/2002 | Lachut |
| 6,887,839 | B2 | 5/2005 | Smith et al. |
| 7,410,936 | B2 | 8/2008 | Lupia et al. |
| 7,449,596 | B2 | 11/2008 | Campbell et al. |
| 7,652,183 | B2 | 1/2010 | Steinbrenner et al. |
| 2008/0139840 | A1 | 6/2008 | Anderson et al. |
| 2013/0281327 | A1 | 10/2013 | Weerasooriya et al. |
| 2018/0057452 | A1 * | 3/2018 | Zhao .................... C07C 309/31 |

FOREIGN PATENT DOCUMENTS

| | | |
|---|---|---|
| CN | 1328251 | 7/2007 |
| CN | 102604620 | 7/2012 |
| CN | 101659861 | 12/2012 |
| CN | 102190604 | 7/2013 |
| CN | 103724235 | 4/2014 |
| CN | 104047014 | 9/2014 |
| CN | 103725268 | 5/2016 |
| DE | 247228 | 7/1987 |
| DE | 10 2004 003310 | 8/2005 |
| EP | 1876172 | 1/2008 |
| GB | 1469442 | 4/1977 |
| RU | 808496 | 10/1992 |
| SU | 591496 | 1/1978 |
| SU | 1036724 | 8/1983 |
| SU | 1293174 | 2/1987 |
| WO | 2012/154376 | 11/2012 |

OTHER PUBLICATIONS

Wang et al., "Synthesis and Interfacial Properties of Dialkybenzensufonates for Producting Low Interfacial Tensions," Tenside Surf. Det., 2008, vol. 45, pp. 25-29.

Ortiz et al., "Effect of Surfactants on Interfacial Films and Stability of Water-in-oil Emulsions Stabilized by Asphaltenes," Journal of Colloid and Interface Science, 2010, vol. 351, pp. 542-555.

Hamdi et al., "Surfactant Based on Aromatic Extract Sulfonate," Ind. Eng. Chem. Res., 1993, vol. 32, pp. 1710-1716.

Aliev et al., "Improvement of Sulfanol Production," Azarbaycan Neft Tasarrufati, 1978, vol. 11, pp. 63-65.

Ashimov et al., "Effect of Aromatic Hydrocarbons of a Kerosine Fraction and its Fractional Composition on the Quality of sulfonal Chloride," Azarbaycan Neft Tasarrufati, 1972, vol. 52, No. 5, pp. 34-36.

Sadykhov et al., "Production of Sulfonate Additives from Baku Petroleum Raw Stock," Khimiya I Tekhnologiya Topliv I Masel, 1977, vol. 12, pp. 29-30.

Strokina et al., "The effect of the Structure of the Hydrocarbon Components of Sulfonated Base Oils on the Sulfonate Properties," Neftepererab Neftekhim (Moscow), 1971, No. 4, pp. 14-15.

Agaeva et al., "Synthesis of surfactants and detergents from natural alkylaromatic hydrocarbons of Azerbaidzhan crude oils," Azarbaycan Neft Tasarrufati, 1964, vol. 43, No. 12, pp. 44-46.

Griesinger et al., "Synthetic detergents from petroleum," Proceedings of the World Petroleum Congress, 1951, Section V, pp. 87-98.

Strokina, "Effect of the fractional composition of raw material on the properties of prepared sulfonates," Neft Gaz Ikh Prod., 1971, pp. 194-195 (Abstract Only).

Kaim et al., "Sulfonation of petroleum fractions and polyalkylbenzenes with gaseous sulfur trioxide," Przemysl Chemiczny, 1991, vol. 70, No. 2, pp. 68-71.

* cited by examiner

ALKYLAROMATIC SULFONATE COMPOSITIONS FROM MIXED HYDROCARBONS

PRIORITY CLAIM

This application claims priority to and the benefit of U.S. Ser. No. 62/382,343, filed Sep. 1, 2016 and is incorporated by reference in its entirety.

FIELD OF THE INVENTION

The present invention relates to processes, systems, and apparatus for making alkylaromatic sulfonate compositions, and such alkylaromatic sulfonate compositions themselves. The alkyl sulfonate compositions may find use as surfactants, in particular in detergent and/or soap applications such as cleaning products, enhanced oil recovery operations, and the like.

BACKGROUND OF THE INVENTION

Alkylaromatic sulfonates are well known surfactants, finding use in various detergent and similar applications. These compositions are typically formed through the alkylation of benzene with partially dehydrogenated paraffins in order to form a linear alkylbenzene (LAB), which comprises a hydrocarbyl radical appended to a benzene ring. The LAB is then subjected to sulfonation, in which a sulfonate group is chemically bonded to a carbon atom in the benzene ring structure of the LAB. The resulting linear alkylbenzene sulfonate (LAS) therefore contains a hydrophilic sulfonate group and a hydrophobic hydrocarbyl portion. Alkylation and sulfonation processes useful for forming LAB and LAS compositions are well known. See, e.g., U.S. Pat. No. 6,887,839.

Petroleum sulfonates are another type of alkylaromatic sulfonate. These compositions are formed from a simpler process of sulfonating crude oil or a crude oil distillation cut. Although the formation is simpler, these compositions typically suffer from significant drawbacks, including a very broad distribution of sulfonated aromatic species and the presence of large amounts of inactive material such as saturates.

SUMMARY OF THE INVENTION

The present inventors have found that through a combination of treatment steps and/or blending, useful alkylaromatic sulfonate compositions can be obtained from hydrocarbon mixtures such as crude oil distillation cuts, without the need for costly dehydrogenation/alkylation processes to form LABs from benzene and paraffins. Furthermore, surprisingly, it has been discovered as part of the present work that certain compounds previously thought to be undesirable in an alkylaromatic sulfonate composition in fact provide advantageous properties in various surfactant applications.

Accordingly, in some aspects, the present invention relates to processes for forming alkylaromatic sulfonate compositions, preferably without alkylation, as well as the alkylaromatic sulfonate compositions themselves. Processes of particular aspects include: (1) obtaining a hydrocarbon mixture; (2) treating the hydrocarbon mixture to obtain a precursor alkylaromatic composition; and (3) sulfonating the precursor alkylaromatic composition, followed by neutralization if necessary, so as to obtain an alkylaromatic sulfonate composition. Processes according to some aspects further include one or more blending steps so as to form a blended alkylaromatic sulfonate composition. For instance, the precursor alkylaromatic composition may be blended with a LAB composition to form a blended precursor alkylaromatic composition which is then sulfonated and, if needed, neutralized, and/or the alkylaromatic sulfonate composition is blended with a LAS composition, to form the blended alkylaromatic sulfonate composition. In processes according to yet other aspects, the (2) treating is optional, such that an untreated hydrocarbon mixture may be sulfonated and then optionally blended with a LAS composition; or the untreated hydrocarbon mixture may be blended with a LAB composition followed by sulfonation of the blended composition (again with optional further blending with a LAS composition).

The hydrocarbon mixture may comprise, or consist essentially of, $C_7$-$C_{30}$ hydrocarbon compounds, preferably $C_{16}$-$C_{28}$ (such as $C_{16}$-$C_{21}$) hydrocarbons; or in some aspects $C_7$-$C_{17}$ hydrocarbon compounds (e.g., for alkylaromatic sulfonate compositions useful in hydrotrope applications); or in further aspects $C_7$-$C_{60}$ hydrocarbon compounds (such broader range useful, e.g., for alkylaromatic sulfonates intended for enhanced oil recovery (EOR) applications). The hydrocarbon compounds comprise both saturated hydrocarbons (e.g., one or more of paraffin, single-ring, and multi-ring saturated hydrocarbons) and unsaturated hydrocarbons (olefins, single ring aromatics, and multi-ring aromatics). The hydrocarbon mixture may advantageously be a crude oil distillation cut, such as a cut having boiling range of 140° C.-420° C., or a cut having narrower boiling range within 140° C.-420° C. (e.g., 260° C.-420° C. or 260° C.-340° C., which ranges may be useful for hydrotrope applications). In yet other embodiments, particularly those in which alkylaromatic sulfonate compositions are desired for EOR applications, broader boiling cuts (e.g., 100° C.-700° C., 120° C.-600° C., or 140° C.-500° C., with ranges from any of the foregoing lows to any of the foregoing highs also contemplated) may be preferred.

In some aspects, the hydrocarbon mixture is further treated to obtain a precursor alkylaromatic composition having a composition tailored for sulfonation. Treating the hydrocarbon mixture may include subjecting the hydrocarbon mixture to any one or more of the following treatment methods: hydrotreating, hydrodesulfurization, catalytic cracking, catalytic reforming, solvent extraction, and solvent dewaxing.

Sulfonation may be carried out using any suitable process now or later known in the art for the attachment of a sulfonate group to an aromatic ring in aromatic hydrocarbons. Such processes include sulfonating the aromatic ring of the aromatic hydrocarbons to form a sulfonic acid, which is then neutralized with base, and purified to yield the alkylaromatic sulfonate.

The alkylaromatic sulfonate compositions of certain aspects may obtain 40-98% surfactant activity. Such compositions according to some embodiments are obtained from a process in accordance with the foregoing description. These compositions may serve as surfactants, and in particular as detergents and/or as components of detergent formulations, e.g., for cleaning compositions and/or for use in enhanced oil recovery operations.

Blended alkylaromatic sulfonate compositions may be formed, such blended sulfonate compositions comprising from 1-99 wt % alkylaromatic compositions according to various embodiments herein, and 1-99 wt % of a LAS composition. The blended alkylaromatic sulfonate compositions of some embodiments are obtained from processes that include blending with LAB and/or LAS compositions in accordance with the foregoing descriptions.

The present inventors have also discovered some alkylaromatic compounds that serve as surprisingly useful blend partners with conventional LAB or LAS compositions, even though one would typically think such blend partners would negatively impact surfactant performance. Accordingly, in yet further aspects, the present invention relates to blends between hydrocarbon mixtures (and/or sulfonates thereof) and LAB and/or LAS compositions. Such hydrocarbon mixtures according to some embodiments may be treated or untreated (e.g., may or may not be subjected to extractions), and may further be highly purified in one or two types of compound (e.g., di-alkylbenzenes and/or alkylated naphthalenes), and may be obtained through separation from a crude fraction or other hydrocarbon mixture, but may also advantageously be obtained by alkylation, or any other means for obtaining such highly purified compounds. These alternatives to conventional LAB and/or LAS compositions may provide substantial advantages to surfactant formulations, including more economical production and/or enhanced surfactant properties such as critical micelle concentration (CMC), wetting, foaming, and the like.

DETAILED DESCRIPTION OF THE INVENTION

Figure 1:
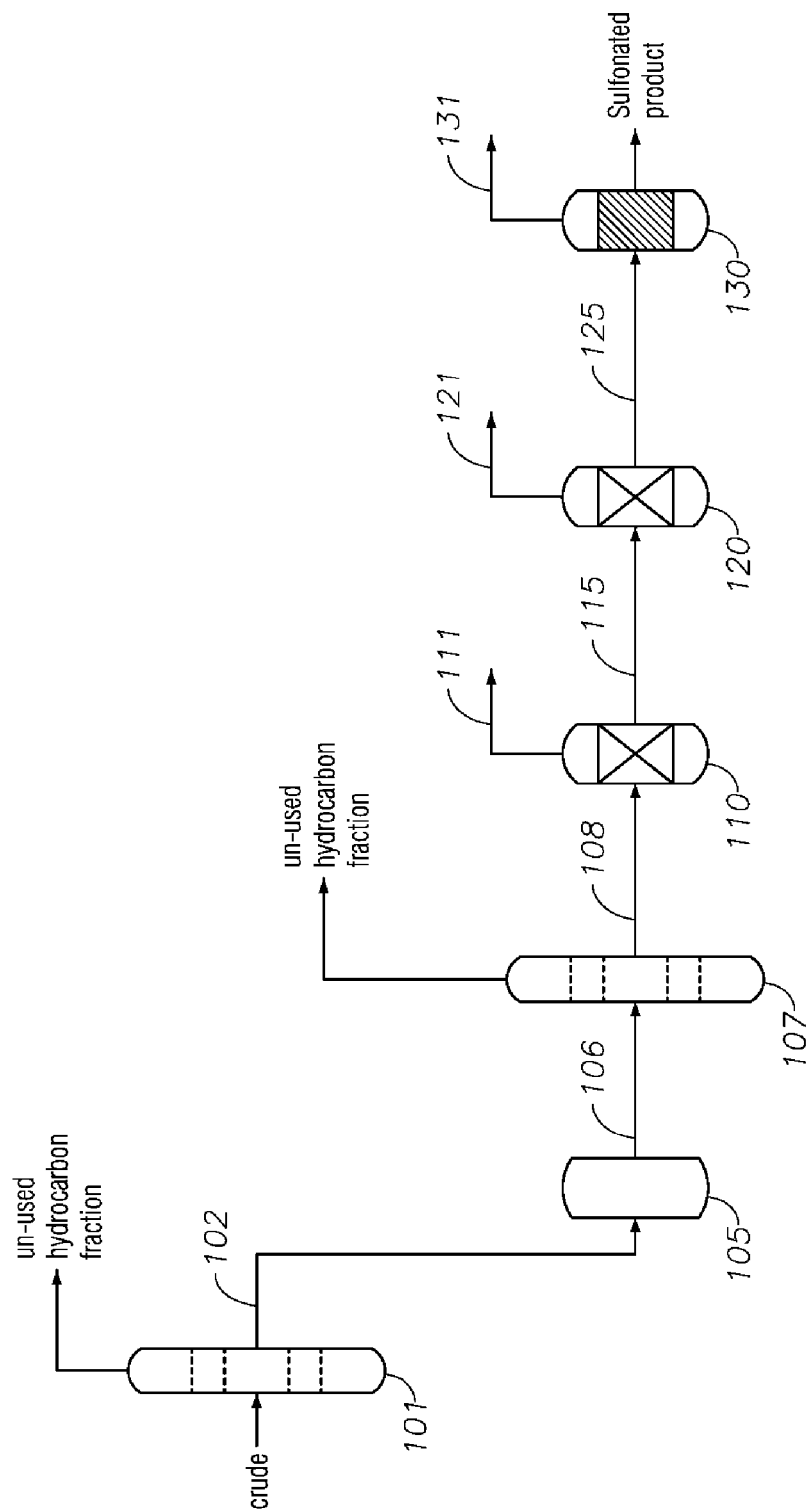
FIG. 1 is a schematic diagram of a process and system for treating hydrocarbon mixtures and sulfonation that may be employed in accordance with some embodiments.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm" as used herein are ppm by weight unless specified otherwise. All concentrations herein are expressed on the basis of the total amount of the composition in question. Thus, the concentrations of the various components of the first mixture are expressed based on the total weight of the first mixture. All ranges expressed herein should include both end points as two specific embodiments unless specified or indicated to the contrary.

Nomenclature of elements and groups thereof used herein are pursuant to the Periodic Table used by the International Union of Pure and Applied Chemistry after 1988. An example of the Periodic Table is shown in the inner page of the front cover of Advanced Inorganic Chemistry, 6$^{th}$ Edition, by F. Albert Cotton et al. (John Wiley & Sons, Inc., 1999).

As used herein, a "carbon number" refers to the number of carbon atoms in a compound. Likewise, a "$C_x$" compound is one having x carbon atoms (i.e., carbon number of x), and a "$C_x$-$C_y$" or "$C_{x-y}$" compound is one having from x to y carbon atoms.

An "alkyl" group or moiety, unless otherwise noted, includes branched, unbranched, cyclic, and acyclic saturated hydrocarbon moieties. A "substituted" hydrocarbon is a hydrocarbon (or hydrocarbon moiety) in which at least one H is replaced with another moiety. For instance, an alkyl-substituted benzene is a benzene with one or more alkyl moieties substituted for one or more pendent H atoms of the benzene.

Various embodiments described herein provide processes for obtaining, and compositions comprising, alkylaromatic sulfonates. These processes advantageously may use crude fractions or other hydrocarbon mixtures as starting material; the hydrocarbon mixture may be treated to tailor its composition, particularly with respect to alkyl aromatic compounds in the hydrocarbon mixture, thereby forming an alkylaromatic precursor composition, which is then sulfonated. Surprisingly, it has been found that many of the resulting sulfonated alkylaromatic compositions exhibit acceptable or even in some cases superior surfactant properties, as compared to the modern conventional alkylaromatic sulfonates, which are formed by alkylating benzene to obtain compositions having a narrow molecular distribution of only a few isomers of particular mono-linear alkyl benzenes. The compositions of many embodiments of the present invention (and/or those obtained through processes in accordance with various embodiments herein) exhibit broader molecular distribution, but still achieve excellent surfactant performance when such diverse compositions are formulated. Furthermore, targeted treatments and other means of tailoring the composition of various hydrocarbon compounds that are subjected to sulfonation according to various embodiments provide surprising performance gains over previously investigated petroleum sulfonates. Many of the aforementioned processes and compositions are described in further detail below, and many more embodiments will be apparent to the skilled artisan upon reading the following description.

Obtaining a Hydrocarbon Mixture

Hydrocarbon mixtures for use in various embodiments of the present invention comprise (or consist essentially of) $C_7$-$C_{30}$ hydrocarbons, preferably $C_{16}$-$C_{28}$ hydrocarbons, such as $C_{16}$-$C_{21}$ hydrocarbons. In yet other embodiments, the hydrocarbon mixture may comprise (or consist essentially of) $C_7$ to $C_{17}$ hydrocarbons (useful, e.g., for alkylaromatic sulfonates intended for hydrotrope applications). In yet further embodiments, the hydrocarbon mixture may comprise (or consist essentially of) a broader range of $C_7$ to $C_{60}$ hydrocarbons (providing alkylaromatics suitable for, e.g., EOR applications). In any of the foregoing embodiments, at least 90 wt %, preferably at least 95 wt %, more preferably at least 99 wt %, of the hydrocarbon mixture is composed of hydrocarbons having any of the aforementioned $C_x$-$C_y$ ranges (i.e., any of the aforementioned numbers of carbon atoms).

According to certain embodiments, the hydrocarbon mixture can be further tailored to suit desired needs of an end product alkylaromatic sulfonate. For instance, a hydrocarbon mixture comprising at least 90, 95, or even 99 wt % $C_{16}$-$C_{21}$ hydrocarbons may be particularly well-suited to obtaining an alkylaromatic sulfonate composition with low-foaming properties, which are preferred for use as a hydrotrope component in a detergent formulation. On the other hand, a hydrocarbon mixture comprising at least 90, 95, or even 99 wt % $C_{22}$-$C_{26}$ hydrocarbons may be well-suited to obtain alkylaromatic sulfonate compositions with critical micelle concentration (CMC) comparable to conventional LAS compositions formed from a process using alkylation of benzenes; such alkylaromatic sulfonate compositions may accordingly be useful as the active surfactant in detergent for cleaning or soaping applications. They may also be employed as lubricating oil surfactants, and/or as components in EOR applications, drilling fluids, and other oilfield applications.

Hydrocarbon mixtures of various embodiments may be obtained from a variety of sources. One preferred source is a crude oil mixture, from which various distillation cuts may be obtained. Thus, processes of some embodiments include obtaining the hydrocarbon mixture as a crude oil fraction. In particular of these embodiments, the hydrocarbon mixture can be alternatively (or additionally) characterized in terms of the boiling point ranges of the constituents of the crude oil fraction. For instance, a hydrocarbon mixture according to some embodiments is a crude oil fraction having boiling point range from 140° C. to 420° C. In certain of these embodiments, such a fraction may be characterized as comprising at least 90, 95, or even 99 wt % $C_{12}$-$C_{26}$ hydrocarbons.

A crude fraction according to such embodiments may be obtained by any suitable separation means known in the art, such as distillation, flashing, or the like.

In particular embodiments (whether the hydrocarbon mixture is characterized by carbon numbers, boiling point range, or both), the hydrocarbon mixture comprises 5-40 wt %, preferably 10-40 wt %, such as 15-35 wt %, or 20-40 wt %, sulfonatable aromatics, with ranges from any of the foregoing low values to any of the foregoing high values also contemplated. The hydrocarbon mixture also comprises 60-95 wt %, preferably 60-90 wt %, such as 65-85 wt %, or 60-80 wt %, compounds other than sulfonatable aromatics (e.g., saturated hydrocarbons such as branched and unbranched alkyl, cycloalkyl, and the like; and also including non-aromatic olefins) and heteroatom-containing compounds (e.g., S-containing and/or N-containing compounds).

Sulfonatable aromatics include single-ring and multi-ring alkylaromatics. Although the initial hydrocarbon mixture may contain non-aromatic olefins, which could technically be sulfonated, in preferred embodiments, such olefins, if present in the hydrocarbon mixture, are removed by treatment (e.g., by hydrotreatment, described in more detail below). Thus, references herein to "compounds other than sulfonatable aromatics" should be taken to include any olefins other than the foregoing aromatics that may be present in the hydrocarbon mixture before or after treatment. In some embodiments, the 5-40 wt %, 10-30 wt %, or 15-25 wt % sulfonatable aromatics of the hydrocarbon mixture are selected from the group consisting of mono-alkyl benzenes (1R alkylaromatics), multi-alkyl benzenes (1.5R alkylaromatics), 2+R alkylaromatics (alkyl-substituted polycyclic aromatics), and any combination of the foregoing. "1R alkylaromatics" or "mono-alkyl benzenes" are benzenes having one alkyl substitution thereon. "Multi-alkyl benzenes" as used herein reference benzenes having two or more alkyl substitutions thereon (e.g., di-alkyl, tri-alkyl, tetra-alkyl benzenes, and the like), and optionally include benzenes in which any two adjacent alkyl substitutions are joined to form a non-aromatic ring fused to the benzene, provided that either the benzene or the fused non-aromatic ring is further alkyl-substituted. Examples of the latter type of compounds include, e.g., mono- or poly-alkyl substituted tetralin (with alkyl substitutions on either or both the benzyl or cyclohexyl ring of the tetralin base structure). Multi-alkyl benzenes may be referred to herein by the shorthand "1.5R alkylaromatics." "Polycyclic aromatics," sometimes referred to herein by the shorthand "2+R alkylaromatics," are polycyclic aromatic hydrocarbons having one or more alkyl substitutions, meaning compounds having 2 or more aromatic rings fused together (with 1 or more alkyl substitutions on any one or more of the aromatic rings). These include alkyl-substituted naphthenes (a 2-ring alkylaromatic), substituted anthracenes (3-ring alkylaromatics), and the like, where the alkyl substitution(s) may be on any one or more of the aromatic rings.

Suitable mono-alkylbenzenes (1R alkylaromatics) include those having structure according to one of Formulas (I) and (II) below:

(I)

(II)

In each of Formula (I) and (II), $R^1$ is $C_1$-$C_{15}$ alkyl, preferably $C_1$-$C_{12}$ alkyl, for instance $C_1$-$C_8$ alkyl. $R^1$ may be branched, but preferably it is either not branched or has branching such that pendent chains (i.e., carbon chains not part of the main, or longest, chain of the moiety) are no longer than 2 carbon atoms. $R^2$ in Formula (II) is $C_1$-$C_8$ alkyl, preferably $C_1$-$C_5$ alkyl. As with $R^1$, $R^2$ may be branched, but preferably it is either not branched or has branching such that pendent chains (i.e., non-main carbon chains) containing no more than 2 carbon atoms.

As noted, the sulfonatable aromatics of the hydrocarbon mixture may also comprise 1.5R alkylaromatic compounds. Such compounds include (i) poly-alkylbenzenes (preferably di- and/or tri-alkylbenzenes) and (ii) alkyl-substituted tetralins.

Di-alkylbenzenes are particularly suitable 1.5R alkylaromatics according to some embodiments. Di-alkylbenzenes of such embodiments include those having structure according to one of Formulas (III), (IV), and (V) below:

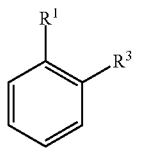

(III)

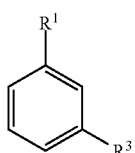

(IV)

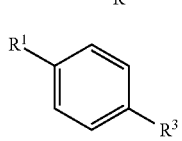

(V)

In Formulas (III)-(V), $R^1$ is as defined in Formulas (I) and (II), provided that the total number of carbon atoms in each formula does not exceed 60 (preferably not to exceed 30, 26, 21, or even 17 in some embodiments). $R^3$ also has the same definitions as $R^1$, although $R^1$ and $R^3$ may be the same or different. Particular examples of di-alkylbenzenes include 1-dodecyl-4-methylbenzene (i.e., a structure according to Formula (V) in which $R^3$ is $C_{10}$ dodecyl, and $R^1$ is a methyl group); 1,4-dioctylbenzene (Formula (V) in which both $R^1$ and $R^3$ are $C_8$ unbranched alkyl).

Similarly, suitable tri-alkylbenzenes include three alkyl substitutions at any three of the carbons along the benzene ring, where each alkyl substitution may be in accordance with the $R^1$ and/or $R^3$ groups discussed above with respect to formulas (III), (IV), and (V), provided that each alkyl group may be the same or different with respect to the other two alkyl groups. For instance, an example of a suitable tri-alkylbenzene is mesitylene (in which the three alkyl substitutions are located on alternating carbons of the benzene ring, and each of the three alkyl substitutions is a methyl, or $C_1$, substitution).

1.5R alkylaromatics of some embodiments also or instead include tetralins (also known as 1,2,3,4-tetrahydronaphthalenes) having 1, 2, 3, or 4 alkyl substitutions at any one or more hydrogens on the tetralin moiety. Preferably, the alkyl-substituted tetralins contain 0, 1, or 2 alkyl substitutions on each of the benzyl ring and the cyclohexyl ring of the tetralin, for instance as shown below in Formula (VI):

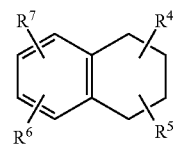

(VI)

In Formula (VI), $R^4$, $R^5$, $R^6$, and $R^7$ are each independently selected in accordance with $R^1$ as discussed with respect to Formulas (I) and (II), provided that the total number of carbons in Formula (VI) does not exceed 60 (preferably 30, 26, 21, or even 17 in some embodiments).

Some particularly useful examples according to yet other embodiments include mono-alkyl tetralins, such as 6-butyl-tetralin (also known as 6-butyl-1,2,3,4-tetrahydronaphthalene). In general, suitable mono-alkyl tetralins may have a $C_1$-$C_{15}$ (preferably $C_1$-$C_{12}$, such as $C_1$-$C_8$) alkyl group substituted at any point on the tetralin. Such alkyl group may be branched, but it is preferably unbranched, or, where branched, pendent chains are no longer than 2 carbon atoms.

Other useful examples of 1.5R alkylaromatic compounds include those having 2 alkyl substitutions in the para-positions on the cyclohexyl ring of the tetralin moiety, i.e., compounds in accordance with Formula (VII) below:

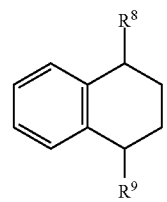

(VII)

In Formula (VII), $R^8$ and $R9^3$ may be the same or different, and are each in accordance with IV and $R^3$ as described with respect to Formulas (III)-(V), provided that the total number of carbon atoms in Formula (VII) does not exceed 60 (preferably not to exceed 30, 26, or even 21 in some embodiments). Examples include 1-decyl-4-methyl-tetralin (i.e., compounds according to Formula (VII) where $R^8$ is decyl and $R^9$ is methyl).

In yet further embodiments, 1.5R alkylaromatics may have 2 alkyl substitutions according to $R^8$ and $R^9$, respectively, at any hydrogen along the benzene and/or along the cyclohexane ring of the compound. That is, the 1.5R alkylaromatics according to such embodiments include structural isomers of compounds according to Formula (VII) in which the tetralin core is retained, but the location(s) of the pendent alkyl groups may be moved.

Sulfonatable aromatics of hydrocarbon mixtures may further comprise 2+R alkylaromatic compounds, i.e., those having 2 or more fused rings and one or more alkyl substitutions. These compounds include alkyl-substituted naphthalenes and anthracenes, particularly those having 1, 2, 3, 4, 5, or 6 alkyl substitutions (preferably from 1 to 4 alkyl substitutions), with each alkyl substitution independently selected from $C_1$-$C_{15}$ alkyl, provided that total number of carbons in the compound does not exceed 60 (preferably not to exceed 30, 26, 21, or even 17 in some embodiments). The alkyl substitutions are each preferably unbranched. Where the alkyl substitution is branched, pendent branches preferably contain no more than 2 carbon atoms.

2+R alkylaromatics of some embodiments are preferably alkyl-substituted naphthalenes. In some embodiments, the alkyl substituted naphthalenes are mono-, di-, tri- or tetra-alkyl substituted naphthalenes, i.e., they have structure in accordance with Formula (VIII) below:

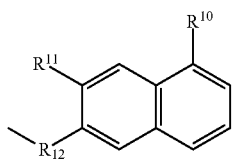

(VIII)

In Formula (VIII), each of $R^{10}$, $R^{11}$, and $R^{12}$ is independently selected from H and $C_1$-$C_{15}$ alkyl, preferably $C_1$-$C_{12}$ alkyl, for instance $C_1$-$C_8$ alkyl, provided that the total number of carbon atoms in Formula (VIII) does not exceed 60 (preferably 30, or in some embodiments 26, 21, or even 17). Furthermore, each of $R^{10}$-$R^{12}$ may be branched, but preferably each is either not branched or has branching such that pendent chains contain no more than 2 carbon atoms. For mono-alkyl-substituted naphthalenes, 2 of $R^{10}$, $R^{11}$, and $R^{12}$ are H; for di-alkyl-substituted naphthalenes, only 1 of $R^{10}$, $R^{11}$, and $R^{12}$ is H; and for tri-alkyl-substituted naphthalenes, none of $R^{10}$, $R^{11}$, and $R^{12}$ are H.

In yet other embodiments, each benzyl ring in an alkyl-substituted naphthalene has 0, 1, or 2 alkyl substitutions, as shown in Figure (IX) below, where $R^{13}$, $R^{14}$, $R^{15}$, and $R^{16}$ are each independently selected in accordance with $R^1$ of Formula (I):

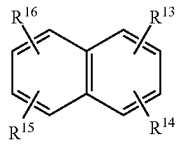

(IX)

In some particular embodiments, the mono-, di-, and/or tri-alkyl-substituted naphthalenes are such that $R^{11}$ and $R^{12}$ are each H or $C_1$-$C_3$ alkyl, and $R^{10}$ is $C_4$-$C_{12}$ (preferably $C_4$-$C_{10}$) alkyl. In such embodiments, each R group is preferably unbranched, or where branched, with pendent chains containing no more than 2 carbon atoms. For instance, then, $R^{11}$ and $R^{12}$ are each $C_1$-$C_3$ alkyl to provide a tri-alkyl-substituted naphthalene according to such embodiments. One particular example of a tri-alkyl substituted naphthalene according to such embodiments includes 6,7-dimethyl-1-(4-methylpentyl)-Naphthalene (i.e., Formula (VIII) where $R^{11}$ and $R^{12}$ are each methyl, and $R^{10}$ is methylpentyl).

In some embodiments, particularly (but not necessarily) those in which the hydrocarbon mixture is obtained from a crude fraction, the sulfonatable portion of the hydrocarbon mixture may exhibit a broad molecular distribution. For instance, the sulfonatable aromatics of the hydrocarbon mixture of such embodiments preferably comprises at least 1R and 1.5R alkylaromatics, and more preferably also comprises 2+R alkylaromatics. The sulfonatable aromatics of the hydrocarbon mixtures of some such embodiments may comprise 35-75 wt % 1R alkylaromatics, 5-75 wt % 1.5R alkylaromatics, and 0-50 wt % 2+R alkylaromatics, provided that the total of all three does not exceed 100 wt % (such wt % s based upon the mass of sulfonatable aromatics in the hydrocarbon mixture).

Alternatively, according to yet other embodiments, the hydrocarbon mixture may be characterized as comprising 1.75-30 wt % (such as 3.5-22.5 wt %, or 5.25-26.25 wt %) 1R alkylaromatics; 0.25-30 wt % (such as 0.5-22.5 wt %, or 0.75-26.25 wt %) 1.5R alkylaromatics; and 0-20 wt % (such as 1-15 wt % or 5-17.5 wt %) 2+R alkylaromatics, such wt % s based on the total mass of the hydrocarbon mixture. Ranges from any of the foregoing low ends to any of the foregoing high ends for each of the 1R, 1.5R, and 2+R alkylaromatics are also contemplated in some embodiments.

In yet other embodiments, the hydrocarbon mixture may be obtained in a manner such that the mixture comprises a substantial majority and/or substantially entirely a desired compound according to the foregoing compounds. Hydrocarbon mixtures according to such embodiments may be particularly useful for blending with LAB or LAS compositions, which will be discussed in more detail below. For instance, a hydrocarbon mixture according to some embodiments may comprise predominantly only one of the types of alkylaromatics (e.g., it may comprise 60-100 wt %, such as 75-95 wt %, or 90-100 wt % of one of the following: 1R alkylaromatics, 1.5R alkylaromatics, or 2+R alkylaromatics, wherein each class of alkylaromatic may contain compounds in accordance with the foregoing descriptions of each). In some embodiments, such hydrocarbon mixtures may consist essentially of the 1R alkylaromatics, 1.5R alkylaromatics, or 2+R alkylaromatics, meaning that only minor amounts (e.g., less than 100 ppm) of sulfonatable aromatics other than the foregoing are present in the hydrocarbon mixture of such embodiments. One or more such hydrocarbon mixtures may thereafter be blended with a LAB compound and sulfonated; or, sulfonated and then blended with a LAS compound, to form a blended alkylaromatic sulfonate composition. As noted, such blending is later described in more detail herein.

Treating the Hydrocarbon Mixture to Obtain a Precursor Alkylaromatic Composition Processes of various embodiments include treating the hydrocarbon mixture, thereby obtaining a precursor alkylaromatic composition with composition tailored for sulfonation. Treatment may include any one or more of various processes known in the art for concentrating a crude oil fraction in sulfonatable aromatics, especially alkylaromatics. A wide variety of treatments are known in the art: for instance, hydrotreating can be used to remove various impurities from a crude oil fraction, such as heteroatom (S- and N-containing) compounds (see, for instance, U.S. Pat. Nos. 3,957,627 and 4,224,144). Other exemplary treatments include solvent extraction to remove separate species of varying solubilities in a given solvent (i.e., relatively more or less polar species). A wide variety of solvents may be used in solvent extraction, targeting compounds of various solubilities; in particular embodiments, extraction is carried out with one or more solvents useful for increasing the concentration of aromatic compounds in a hydrocarbon composition. Other treatment options include catalytic reforming and dehydrogenation, e.g., to convert alkanes into aromatics (see, for instance, U.S. Pat. Nos. 2,915,455; 5,011,805; 5,885,439; and 6,773,580).

Processes according to various embodiments include treating the hydrocarbon mixture to arrive at a desired mixture of components. For instance, some embodiments include treating the hydrocarbon mixture so as to obtain a precursor alkylaromatic composition comprising sulfonatable aromatics at a wt % greater than the wt % of sulfonatable aromatics in the untreated hydrocarbon mixture. For instance, a precursor alkylaromatic composition, following treatment, may comprise sulfonatable aromatics within the range from a low of 30, 35, 40, 45, 50, 55, or 60 wt %, to a high of 62, 65, 75, 80, 85, 90, or 95 wt %. In some preferred embodiments, the precursor alkylaromatic compound comprises an even higher wt % of sulfonatable aromatics (e.g., ranging from a low of 75, 80, or 85 wt % to a high of 85, 90, 95, or even 99 wt %, provided the high end of the range is greater than the low end).

Solvent extractions that increase the wt % of aromatic compounds (and/or decrease the wt % of other compounds, such as saturated compounds) are particularly useful for increasing the wt % of sulfonatable aromatics. In particular embodiments, treatment includes subjecting the hydrocarbon mixture to 1, 2, 3, 4, or 5 such solvent extractions, thereby increasing the wt % of sulfonatable aromatics in the precursor alkylaromatic composition relative to the untreated hydrocarbon mixture. Solvent extractions that increase aromatic content in a hydrocarbon composition include, but are not limited to, N-methyl-2-pyrrolidone (NMP) extraction, sulfolane extraction, furfural extraction, and/or extraction using dimethyl sulfoxide (DMSO), sulfur dioxide (SO2), sulfuric acid, and/or phenol. Also or instead, such solvent extractions can be carried out so as to tailor aromatics (e.g., increase the relative amount of 1R, 1.5R, or 2+R alkylaromatics) in the composition, and/or to reduce overall aromaticity. For instance, in some instances, a mild NMP extraction may be used to remove 2+R alkylaromatics prior to extracting the obtained raffinate more severely to obtain the 1R and 1.5R alkylaromatics. Methods for carrying out such extractions are well known in the art. See, for instance, U.S. Pat. Nos. 2,079,885; 2,698,276; 3,338,823; 3,544,453; 3,556,991; 3,567,627; 3,723,256; 3,929,616; 4,013,549; 4,053,369; 4,571,295; 4,909,927; 5,041,206; 6,866,772; and 7,078,580; see also US Patent Publication No. 2016/0075954; and F. Lee, et al., "*Two Liquid-Phase Extractive Distillation for Aromatics Recovery*," Ind. Eng. Chem. Res. (26) No. 3, pp. 564-573, (1987). Suitable solvent extractions for increasing the aromatic content of a hydrocarbon mixture will be readily apparent to the skilled artisan in view of the present disclosure. In some particular embodiments, NMP extraction may be preferred. Advantages of NMP extraction include higher selectivity for desired molecules, less toxic solvent, and relatively easier recovery of the solvent from the oil.

In general, the greater the number of solvent extractions, the higher the wt % of aromatics (and therefore higher wt % of sulfonatable aromatics) in the precursor alkylaromatic composition. For instance, an untreated hydrocarbon mixture of some embodiments may comprise 15-25 wt % sulfonatable aromatics. Treatment according to such embodiments including one or more NMP extractions may yield a precursor alkylaromatic composition comprising: 35-50 wt % sulfonatable aromatics (1 extraction); 45-55 wt % sulfonatable aromatics (2 extractions); 55-75 wt % sulfonatable aromatics (3 extractions); and 65-85 wt % sulfonatable aromatics (4 extractions).

However, while increasing number of extractions increases the wt % of sulfonatable aromatics in the precursor alkylaromatic composition, it also reduces the overall yield of the hydrocarbon feed provided to sulfonation. Further, greater number of extractions means greater expense and complexity of the system. It is therefore desired to find a balance; hence, 1, 2, or 3 extractions are preferred in certain embodiments.

Extraction according to particular embodiments employs not only a particular solvent, but also extraction conditions suitable to obtain a desired molecular distribution among the sulfonatable aromatics. For instance, NMP extraction can be carried out at mild, moderate, or severe conditions. Mild, moderate, or severe conditions refer to the yield of the extract phase. Lower extract yields, for example less than 10 vol % of feed, are obtained under mild conditions. Higher extract yields, for example greater than 10 vol % of feed, are obtained at more severe conditions. Any combination of conditions such as solvent treat ratio, water content in solvent, and extractor temperature can be used to increase or decrease the amount of molecules which partition into the extract phase to adjust the severity between mild, moderate, and severe. In general, increasing treat rate, increasing temperature, and decreasing water content will each increase the severity of the extraction.

Depending on the solvent selected and extraction severity, a different distribution among 1R, 1.5R, and 2+R alkylaromatics may be obtained within the sulfonatable aromatics of the precursor alkylaromatic composition. For instance, mild NMP extraction may yield a raffinate precursor alkylaromatic composition having fewer 2+R alkylaromatics relative to 1R and 1.5R alkylaromatics, while severe NMP extraction of the raffinate may result in greater relative removal of 1R alkylaromatics. Although many possibilities exist for adjusting relative concentration of 1R, 1.5R, and 2+R alkylaromatics using various extraction techniques, the following general guidance is noted:

Extractions (solvent/conditions) to decrease 1R relative wt %: ≥100% treat rate (the amount of solvent, in vol %, used relative to the volume of hydrocarbon feed; greater than 100% means to employ a greater volume (or volumetric feed rate) of solvent than feed for the treatment); ≤1 wt % water in solvent; temperature ≥25° C.;

Extractions (solvent/conditions) to decrease 1.5R relative wt %: ≥100% treat rate; ≤1 wt % water in solvent; temperature ≥25° C.;

Extractions (solvent/conditions) to decrease 2+R relative wt %: ≤100% treat rate; ≤1 wt % water in solvent; temperature ≤25° C.

According to some embodiments, other treatment methods may be employed, alone or in combination with extraction. For instance, hydrotreating may be employed prior to, between, or after, any one or more of the 0, 1, 2, 3, 4, or 5 extractions so as to remove heteroatoms (especially N- and S-containing compounds). Preferably, hydrotreatment is carried out prior to the 0, 1, 2, 3, 4, or 5 extractions. Also, the hydrotreatment is preferably carried out using relatively low temperature (300° C. or less) and/or high pressure (200 psig or greater) with a catalyst having metals sites.

Some processes also or instead include reforming and dehydrogenation to convert a fraction of alkanes (e.g., in particular to convert cycloalkanes and/or isoparaffins) in the hydrocarbon mixture to aromatics (especially alkylaromatics). In certain embodiments, one or more extraction effluent streams rich in saturated hydrocarbons (e.g., hydrocarbons separated from the hydrocarbon mixture using any one or more extractions) may be catalytically reformed and dehydrogenated so as to convert at least a portion of the saturates (especially cycloalkanes and/or isoparaffins) to aromatics (especially alkylaromatics). Any suitable reforming/dehydrogenation process may be employed, although in some particular embodiments, mild reforming (350° C.-400° C., <400 psig, 1-2 hr$^{-1}$ LHSV, Re/Pt catalyst) may be utilized. Preferably, where reforming is used in combination with extraction, the reformate product is supplied to one or more solvent extractions (e.g., by recycling or passing to a downstream extraction).

It should further be noted that any of various treatments may be intermingled with one or more distillation steps (e.g., one or more distillation steps used to obtain the hydrocarbon fraction), particularly where processes in accordance with some embodiments are integrated into existing refinery operations. For instance, a first distillation may be followed by a first hydrotreatment, in turn followed by a second distillation, before the hydrocarbon mixture (containing a mixture of hydrocarbons in accordance with the above descriptions) is obtained. Thus, unless specifically noted otherwise, it should be understood that there may be some degree of commingling between (i) processes in connection with obtaining the hydrocarbon mixture of various embodiments, and (ii) treatment processes of various embodiments. Nonetheless, in particular embodiments, one or more distillations may be carried out before and/or after one or more hydrotreatments; any extractions employed as part of treatment are then carried out following all distillations and hydrotreatments.

FIG. 1 provides one example of a treatment process that may be employed in accordance with various embodiments. In FIG. 1, a hydrocarbon mixture 102 is obtained as a crude fraction following distillation 101. The hydrocarbon mixture 102 is passed to hydrotreatment 105 to provide a hydrotreated stream 106, which is passed to distillation 107. An alkylbenzene fraction 108 is obtained and passed to a first solvent extraction 110. According to the process shown in FIG. 1, first solvent extraction 110 is carried out using NMP at mild conditions (66% treat rate, 0.5 wt % $H_2O$ in solvent, 25° C.). The first solvent extraction 110 serves to remove 2+R alkylaromatics in effluent 111, leaving an intermediate hydrocarbon stream 115 concentrated in 1R and 1.5R alkylaromatics, which is in turn provided to second solvent extraction 120. The second solvent extraction 120 as shown in FIG. 1 is operated at severe conditions (e.g., 225% treat rate, 0.5 wt % $H_2O$ in solvent, 25° C.) to provide a second extraction product 125 further concentrated in aromatics (in particular 1R and 1.5R alkylaromatics), with an effluent 121 rich in saturated hydrocarbons drawn off. The second extraction product 125 is provided as the precursor alkylaromatic composition to sulfonation 130, from which the alkylaromatic sulfonate product 135 is produced. An oil-rich phase 131 is withdrawn from sulfonation, as described in more detail below.

Figure 2:
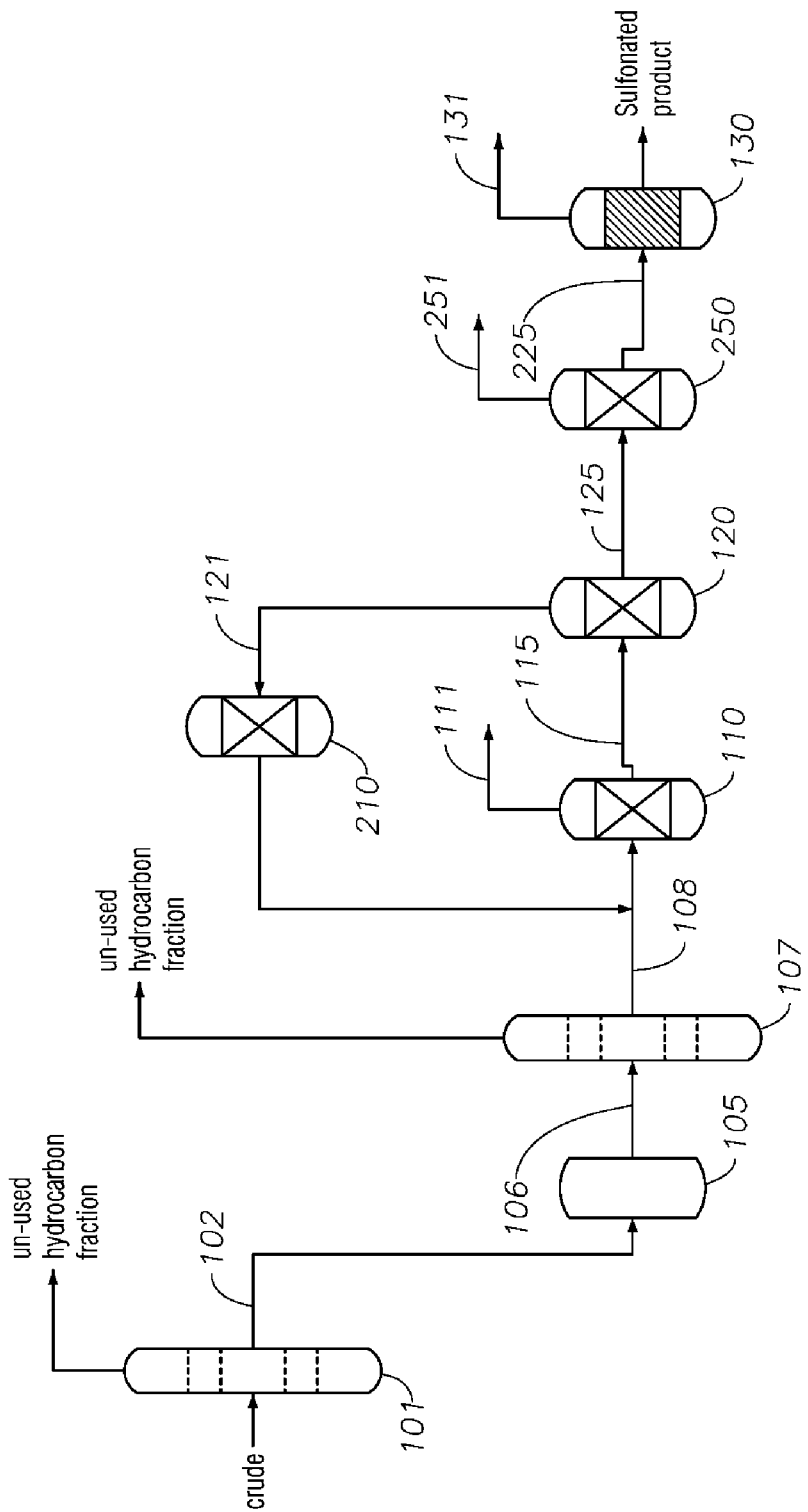
FIG. 2 is a schematic diagram of one alternative process and system for treating hydrocarbon mixtures and sulfonation that may be employed in accordance with other embodiments.

FIG. 2 illustrates two modifications of the process shown in FIG. 1, in accordance with yet other embodiments. First, the effluent 121 rich in saturated hydrocarbons is provided to a reforming system 210 in which at least a portion of the saturated hydrocarbons of the effluent 121 are converted to aromatics, from which is obtained an aromatic-concentrated recycle 215 to be provided to the first solvent extraction 110. Second, the second extraction product 125 is subjected to one or more additional extractions 250, in which the product 125 is further concentrated in aromatics (particularly 1R alkylaromatics) following removal of one or more effluents 251 rich in saturated hydrocarbons, thereby providing a further treated product 225 which is sent to sulfonation 130 as the treated hydrocarbon stream.

Further guidance in targeting particular types of aromatic compound for retention and/or removal from the precursor alkylaromatic composition is provided in the Examples section below. Other methods for targeting particular types of aromatic compounds will be apparent to the ordinarily skilled artisan in view of the teachings of the present disclosure.

Treatment with solvent extraction according to some embodiments may further include, following any one or more extractions, distillation or other separation so as to remove the solvent(s) from the treated hydrocarbon. For example, in a solvent recovery tower, water can be added to raffinate or extract phases at temperatures between 25° C. and 90° C. The oil will separate from the water/solvent and form a light top phase. The product oil can be collected by siphoning from the top of the solvent recovery tower. The bottom heavy phase (water/solvent) can be collected by siphoning from the bottom of the solvent recovery tower. To recover the solvent, one may bring the water/solvent to >90° C. (such as >100° C.) in order to boil off the water.

Accordingly, in general, the hydrocarbon mixture of some embodiments is subjected to one or more treatments such that the precursor alkylaromatic composition comprises 0-40 wt %, such as 5-40 wt % (preferably 0-20 or 0-25 wt %, such as 10-20 or 10-25 wt %) 2+R alkylaromatic compounds; 10-45 wt % (preferably 15-30 wt %) 1.5R alkylaromatic compounds; and 15-50 wt % (preferably 15-35, such as 10-25 wt %) 1R alkylaromatic compounds, said wt % s determined on the basis of the precursor alkylaromatic composition. Ranges from any of the aforementioned low ends to any of the aforementioned high ends are also contemplated for each of the 2+R, 1.5R, and 1R alkylaromatics. Furthermore, in each of the aforementioned embodiments, any one or more, and preferably each, of the 1R, 1.5R, and 2+R alkylaromatics is present in the precursor alkylaromatic composition at a wt % greater than each such compound was present in the hydrocarbon mixture (i.e., prior to the one or more treatments). Further, the precursor alkylaromatic composition may have a broad molecular distribution among the 1R, 1.5R, and 2+R alkylaromatic compounds, meaning that the wt % s of each of the 1R, 1.5R, and 2+R alkylaromatic compounds in the precursor alkylaromatic composition are similar to each other. For instance, in some embodiments, the wt % of the 1.5R alkylaromatics in the precursor alkylaromatic composition (1) differs from the wt % of the 1R alkylaromatics in the precursor alkylaromatic composition by no more than 10 wt %, and (2) differs from the wt % of the 2+R alkylaromatics in the precursor alkylaromatic composition by no more than 10 wt %.

Other, more particular, molecular distributions may be targeted in various embodiments; in some of these embodiments, a different application of the sulfonated product of the precursor alkylaromatic composition may be contemplated, depending upon the molecular distribution. Some sample distributions, and potential applications according to some such embodiments, are summarized in Table 1 below.

Sulfonation

The precursor alkylaromatic composition according to various embodiments may be subjected to sulfonation in order to obtain an alkylaromatic sulfonate composition.

Sulfonation may be carried out by any suitable process known in the art for sulfonating aromatic compounds so as to substitute a sulfonate group for a hydrogen atom on the aromatic ring of such compound. For instance, sulfonation may conveniently be carried out according to conventional sulfonation methods utilized for commercial linear alkyl benzene (LAB) compositions. Such methods include contacting the precursor alkylaromatic composition with a sulfonating agent such as sulfuric acid or a sulfur trioxide compound. Suitable sulfur trioxide compounds include oleum, otherwise known as fuming sulfuric acid, which comprises sulfur trioxide (typically 10-25%) in sulfuric acid; other suitable sulfur trioxide compounds include an $SO^3$-air mixture. Reaction between the precursor alkylaromatic composition and the sulfonating agent produces an alkylaromatic sulfonic acid, in which an $SO_3$ moiety is appended to the aromatic ring (or, where multiple aromatic rings are present, any one or more of the aromatic rings may have an $SO_3$ moiety appended thereto).

The acid may exist as a cationic species or as the acid. Either way, the composition is neutralized using any of a variety of bases. Examples of suitable bases include sodium, potassium, calcium, magnesium, ammonia, amines (e.g., isopropylamine, methylamine, triethanolamine, etc.), and salts thereof. For instance, aqueous NaOH, KOH, $Ca(OH)_2$ or the like may be used for neutralization of the alkylaromatic sulfonic acid. The result is a composition comprising the alkylaromatic sulfonate and/or salts thereof. That is, since the alkylaromatic sulfonate contains a sulfonate moiety, it is anionic and therefore ionically bonds to the neutralization salt (e.g., Na). References herein to an "alkylaromatic sulfonate" are therefore intended to include both the anionic sulfonate species and its neutral salt (e.g., sodium salt, potassium salt, ammonium salt, or the like). Indeed, when used in applications such as household detergents, industrial detergents, EOR applications, and the like, the alkylaromatic sulfonate will likely exist in its neutral salt form.

Following neutralization, the composition may be purified (e.g., removal of saturated sulfate salt solution, such as $Na_2SO_4$ where sodium salts are used for neutralization; as well as filtration, centrifuging, washing, drying, and/or other methods for removing the solid sulfonate product from aqueous solution).

Figure 3:
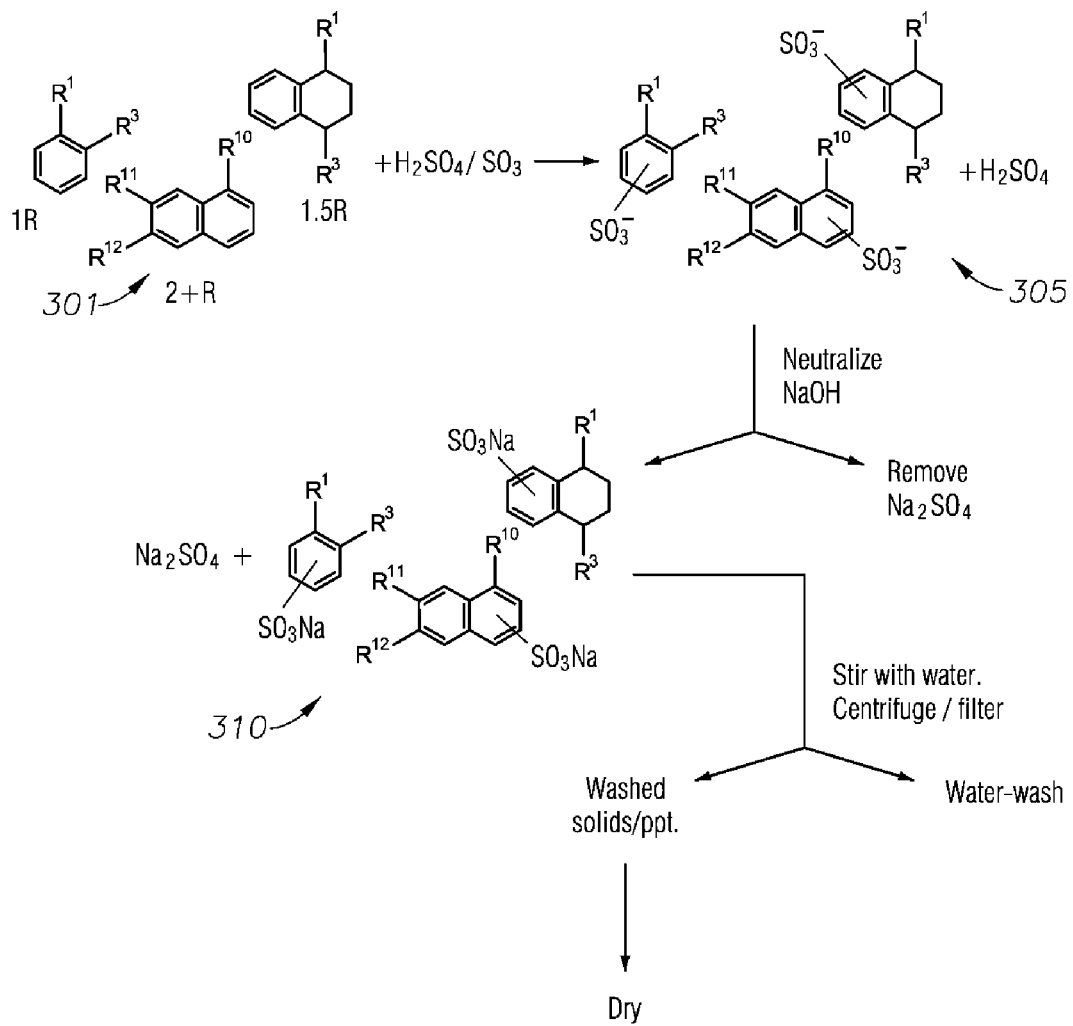
FIG. 3 is an illustration of a reaction process that may be suitable for sulfonation in accordance with some embodiments.

FIG. 3 is an illustration of an example synthetic route for sulfonation of precursor alkylaromatic compositions according to some embodiments. Such a process is particularly useful for mixtures of 1R alkylaromatic compounds. This process may be particularly suited for batch sulfonation, although it may be adapted to continuous sulfonation if desired (for instance, $SO_3$ in air may be used for continuous sulfonation). Per FIG. 3, precursor alkylaromatic composition 301 may comprise a mixture of 1R, 1.5R, and 2+R alkylaromatics (with non-limiting examples of such compounds illustrated in FIG. 3, and with 1R alkylaromatics preferred). These are contacted with oleum to form the sulfonic acid 305, then neutralized with dilute NaOH. Saturated $Na_2SO_4$ solution is removed, leaving the salt of the alkylaromatic sulfonate 310. The salt is purified by stirring with water, centrifuging, and filtering to remove the water wash. The washed solids 315 are further dried (e.g., at 75° C.) to obtain the alkylaromatic sulfonate product.

In yet other embodiments, the sulfonation process may be modified to account for differences that may exist between more typical commercial LABs and precursor alkylaromatic compositions in accordance with some embodiments (e.g., the presence of 1.5R and 2+R alkylaromatics in addition to 1R alkylaromatics). In particular, sulfonation according to some embodiments may include (1) removing an upper oil phase from the alkylaromatic sulfonic acid composition (e.g., by gravity separation) prior to or concurrent with neutralization (such oil phase comprising from 10-60, such as 20-50, wt % of the sulfonic acid composition), and (2) modified purification to account for the fact that sulfonated alkylaromatic salts according to some embodiments are water soluble. Thus, solvent extraction and separation from the solvent may be preferred to remove the active sulfonated product from aqueous solution, rather than filtration and other solid/liquid separation techniques. Suitable sulfonation product solvents for this product extraction include isopropyl alcohol and other volatile solvents in which the sulfonates are soluble and sodium sulfonate is not.

Figure 4:
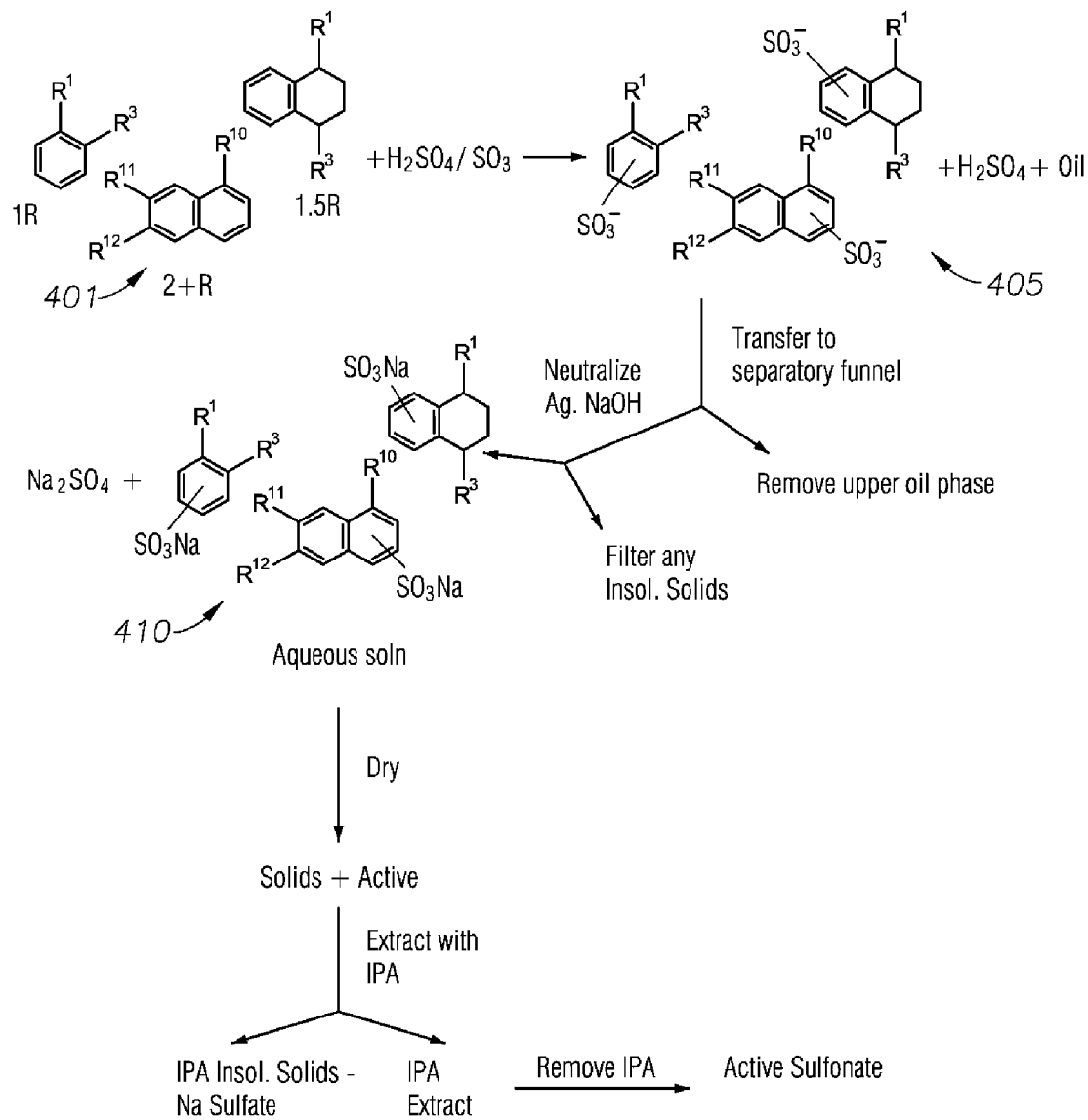
FIG. 4 is an illustration of another reaction process that may be suitable for sulfonation in accordance with other embodiments.
Figure 5:
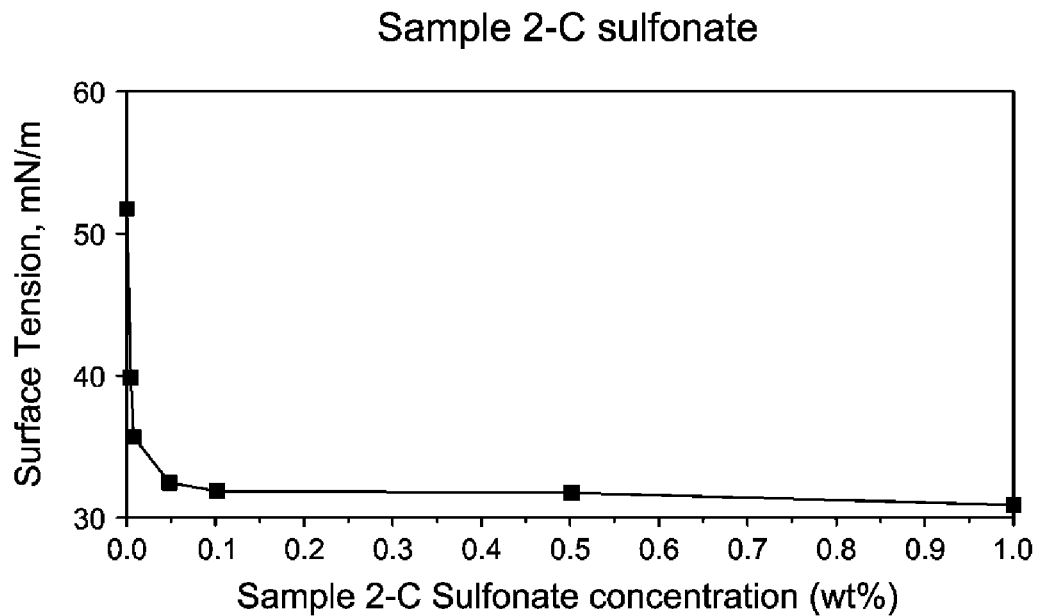
FIG. 5 is a graph of surface tension (mN/m) vs. sulfonated sample concentration in water (wt %) used to determine CMC values for samples in connection with Example 2.
Figure 6:
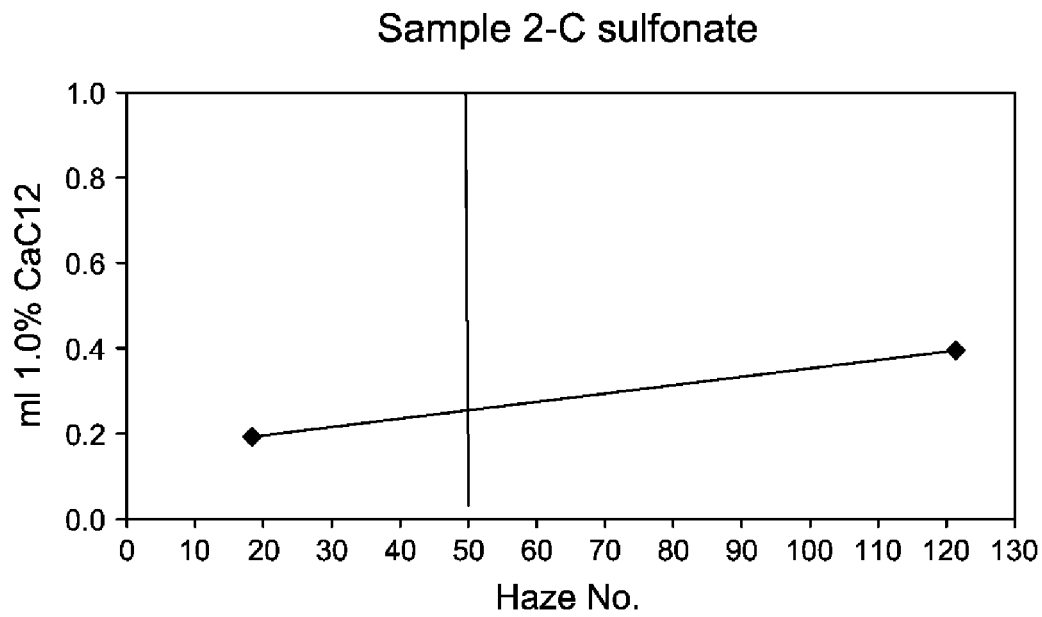
FIG. 6 is a graph of the volume of 1% $CaCl_2$ solution added to sample solutions in accordance with Example 2 vs. Haze No., used to determine Ca tolerance in connection with Example 2.
Figure 7:
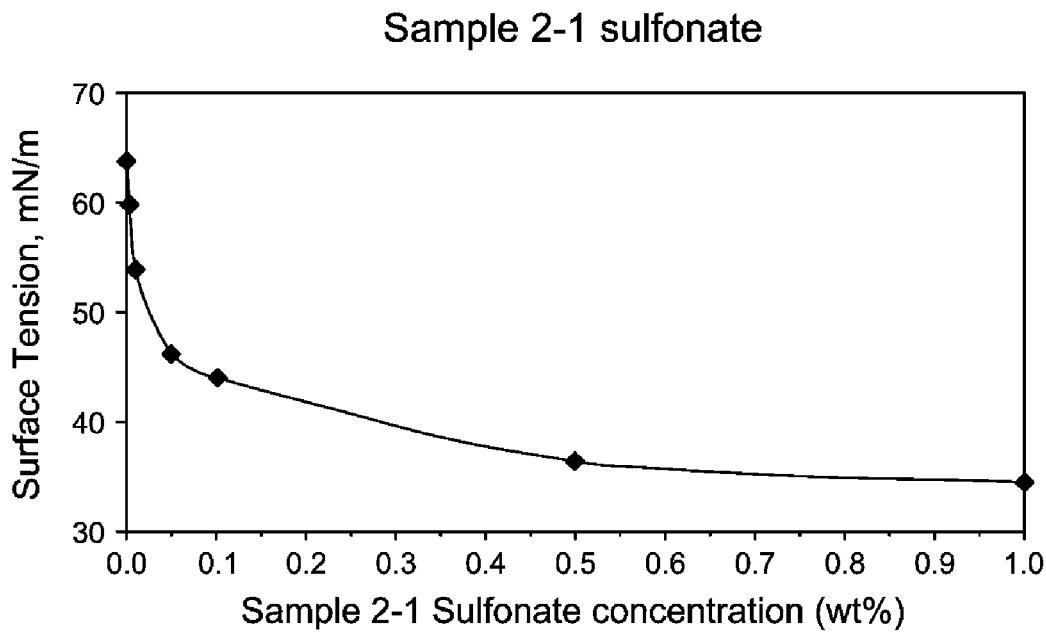
FIG. 7 is a graph of surface tension (mN/m) vs. sulfonated sample concentration in water (wt %) used to determine CMC values for samples in connection with Example 2.
Figure 8:
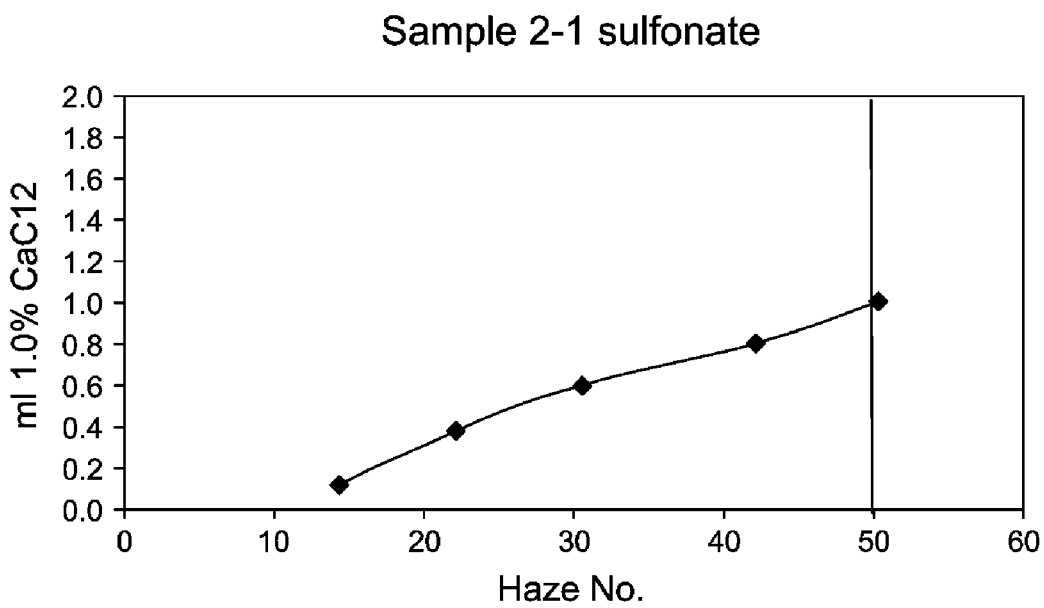
FIG. 8 is a graph of the volume of 1% $CaCl_2$ solution added to sample solutions in accordance with Example 2 vs. Haze No., used to determine Ca tolerance in connection with Example 2.
Figure 9:
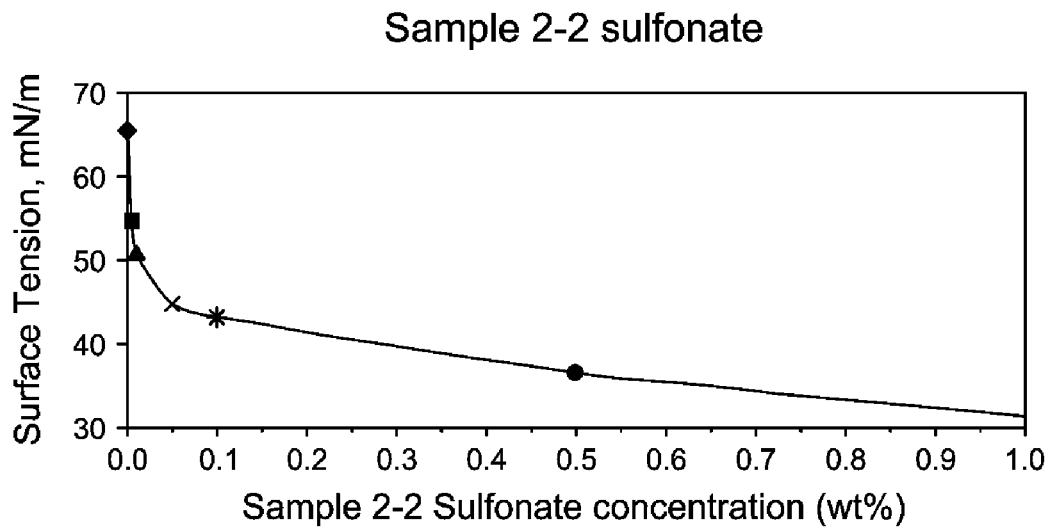
FIG. 9 is a graph of surface tension (mN/m) vs. sulfonated sample concentration in water (wt %) used to determine CMC values for samples in connection with Example 2.
Figure 10:
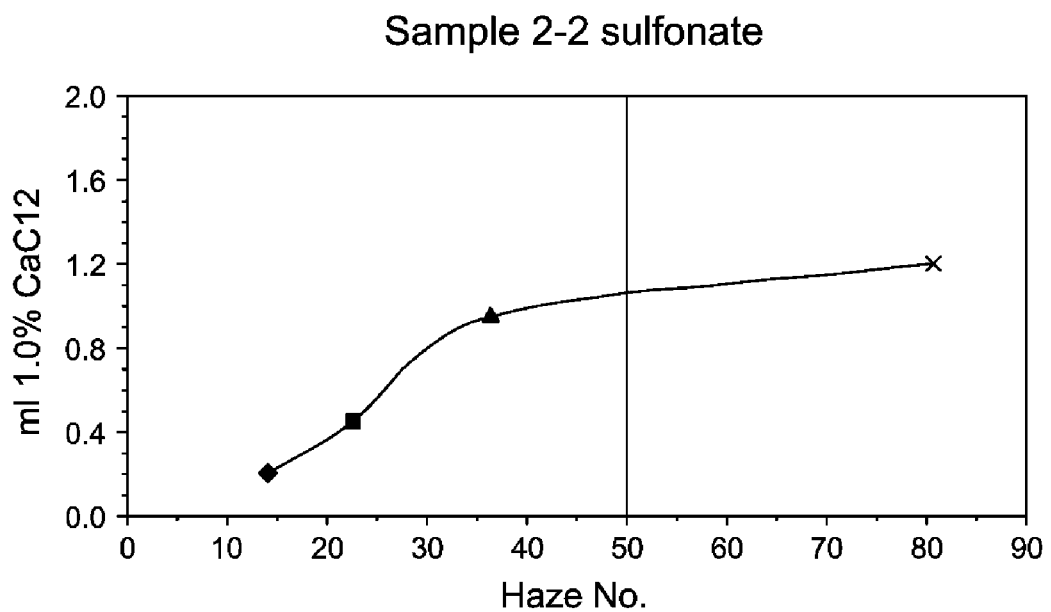
FIG. 10 is a graph of the volume of 1% $CaCl_2$ solution added to sample solutions in accordance with Example 2 vs. Haze No., used to determine Ca tolerance in connection with Example 2.
Figure 11:
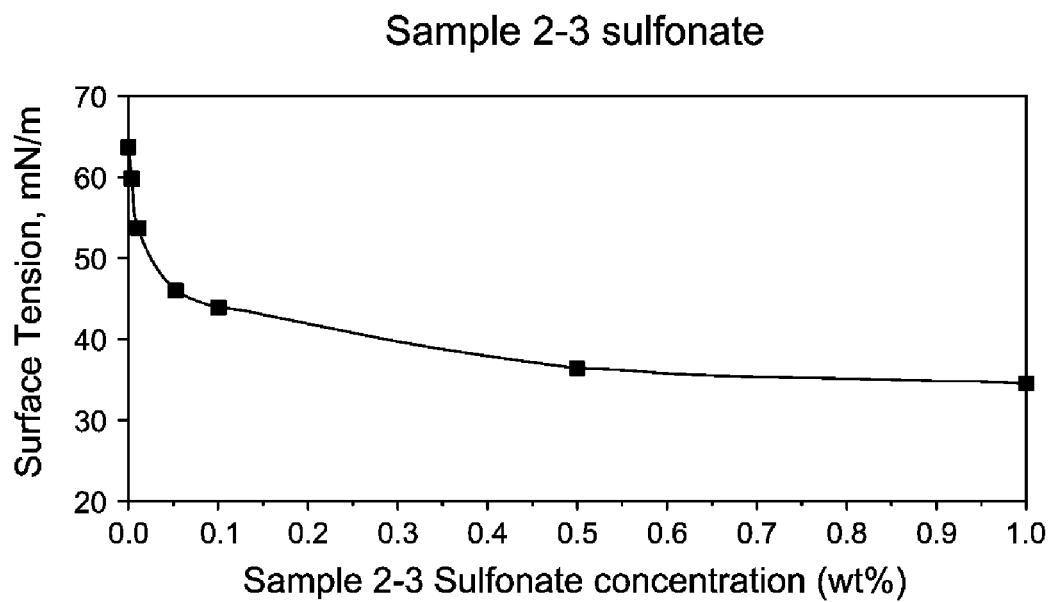
FIG. 11 is a graph of surface tension (mN/m) vs. sulfonated sample concentration in water (wt %) used to determine CMC values for samples in connection with Example 2.
Figure 12:
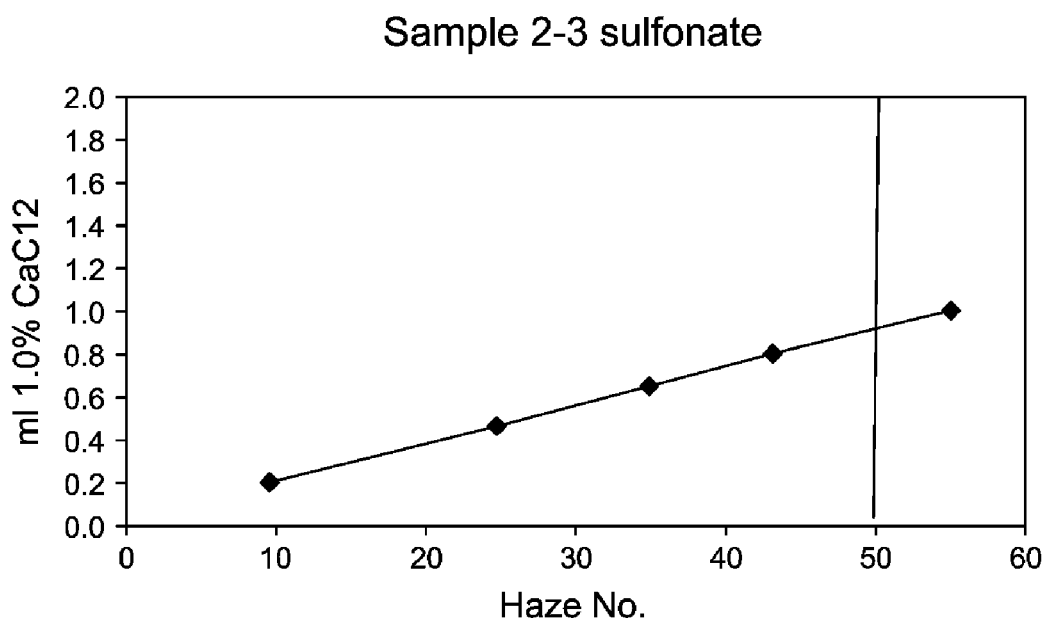
FIG. 12 is a graph of the volume of 1% $CaCl_2$ solution added to sample solutions in accordance with Example 2 vs. Haze No., used to determine Ca tolerance in connection with Example 2.

Sulfonation processes according to such embodiments are illustrated in FIG. 4. Sulfonation in embodiments in accordance with FIG. 4 may include: contacting the alkylaromatic precursor composition 401 with sulfonating agent (e.g., oleum, as shown in FIG. 4) to obtain the alkylaromatic sulfonic acid composition 405; separating an oil phase from the acid composition 405; and neutralizing the acid composition 405 with base (e.g., aqueous NaOH, as shown in FIG. 4) to obtain a crude alkylaromatic sulfonate composition 410. Purification of the crude alkylaromatic sulfonate composition according to such embodiments may include drying (e.g., filtration) to obtain a wet solid, and product extraction to obtain the alkylaromatic sulfonate composition (shown in FIG. 4 to be carried out using isopropyl alcohol (IPA) as a solvent).

Alkylaromatic Sulfonate Compositions

Alkylaromatic sulfonate compositions of some embodiments are preferably obtained by processes according to any one or more of the foregoing embodiments. Alkylaromatic sulfonate compositions of various embodiments may comprise the sulfonate and/or sulfonate salt of any one or more of the previously described 1R, 1.5R, and 2+R alkylaromatic compounds (such compounds may also be referred to herein as 1R alkylaromatic sulfonates, 1.5R alkylaromatic sulfonates, and/or 2+R alkylaromatic sulfonates, respectively). More particularly, alkylaromatic sulfonate compositions may comprise the sulfonate and/or sulfonate salt of any one or more compositions in accordance with Formulas (I)-(VIII).

The alkylaromatic sulfonates of some such embodiments may be particularly useful as surfactants, and in particular as detergents (e.g., in cleaning applications and/or for enhanced oil recovery operations), or as industrial detergents, enhanced oil recovery (EOR) applications, as demulsifiers, and the like.

Alkylaromatic sulfonates according to some embodiments have surfactant activity within the range from 40 to 98%, such as within a range from a low of any one of 40, 50, 60, 70, and 75% to a high of any one of 70, 75, 80, 85, 90, 95, and 98%, provided the high end of the range is greater than the low end. As used herein with respect to alkylaromatic sulfonate compositions, "activity" or "surfactant activity" refers to the percent of sulfonates in the composition, as determined according to ASTM D3049. A sample of the composition is titrated with hyamine. In general, activity $A=((V \times N \times EW) \times 100)/(W)$, where V is volume of hyamine (ml) needed to titrate the sample; N is the normality of hyamine titrant (meq/ml); EW is the equivalent weight of the sample (mg/meq); and W is the weight (mass) of the sample (mg).

The alkylaromatic sulfonates of some embodiments may also or instead exhibit any one or more of the following surfactant and/or detergent properties:

Critical micelle concentration (CMC) within the range from 0.01-1.0 wt %, preferably within the range from 0.01-0.5 wt %, more preferably within the range from 0.01-0.05 wt %. CMC is determined in accordance with ISO 4311, utilizing the DuNouy Ring method. Various serial dilutions of the product are made in deionized water (starting with a 1% solution in deionized water, diluted down until no measurable difference in surface tension is detected compared to distilled water). Surface tensions are plotted against the concentration. Surface tensions are measured with a BZY Series Automatic Surface Tension meter using the Du Nouy Ring method, which is based upon measuring the force required to detach a platinum wire ring from a liquid surface or from the interface between two liquids (in the case of interfacial tension). See du Noüy, Pierre Lecomte, "*An Interfacial Tensiometer for Universal Use*," The Journal of General Physiology, 7 (5): pp. 625-633 (1925). The region where the curve shows no further decrease in surface tension with increasing concentration is designated the CMC.

Draves wetting within the range from 100-600 sec; preferably from 100-200 sec. Unless otherwise specified herein, Draves wetting is determined in accordance with ASTM D2281-10.

Ross-Miles Foam height (initial) within the range from 10-75 mm (initial), preferably within the range from 10-50 mm (initial), more preferably within the range from 10-40 mm (initial), or even 10-25 mm (initial). In terms of Ross-Miles Foam Height (after 5 min): within the range from 10-55 mm, preferably within the range from 10-50, more preferably within the range from 10-25 mm Unless otherwise specified herein, Ross-Miles foam height is determined at initial time and after 5 min in accordance with ASTM D1173-07.

Interfacial tension (IFT) of a 0.10 wt % solution of the sulfonate in distilled water within the range from 5.5-9.5 mN/m; preferably from 5.5-7.5 mN/m, more preferably from 5.5-7.0 mN/m. Also or instead, such compositions may exhibit IFT of a 0.5 wt % solution of the sulfonate in distilled water within the range from 3.5-6.0, preferably 3.5-5.5 mN/m. IFT is determined using a 0.1 wt % solution of sample in distilled water. The interfacial tension is measured against mineral oil in accordance with ASTM D971, using a BZY Series Automatic Surface Tensionmeter following the Du Nouy Ring Method (see description of CMC measurements, above). The solution of sulfonate in water is placed in a glass beaker and the platinum ring is then immersed below the surface. Mineral oil is poured on top. The ring is then raised through the solution:oil interface and the force necessary to detach it from the bottom aqueous phase is measured. Deionized water is used as the comparator aqueous phase against which IFT values for the solutions are compared.

Calcium tolerance (which may otherwise be referred to as "hard water tolerance") within the range from 50-90 mg Ca/g sulfonate (i.e., grams of the alkylaromatic sulfonate); preferably within the range from 60-90 mg Ca/g sulfonate; more preferably within the range from 65-90 mg Ca/g sulfonate. Unless specifically noted otherwise herein, calcium tolerance is determined by adding $CaCl_2$ to a sample of X grams of the alkylaromatic sulfonate until a turbidity of 50 nephelometric turbidity units (NTU) is obtained, as measured according to ISO 7027 using a LaMotte 2020E turbidity meter (or equivalent suitable for ISO 7027 measurements). The amount of $CaCl_2$ (mg) necessary to obtain the 50 NTU turbidity is recorded, and divided by the X grams of alkylaromatic sulfonate sample to which the $CaCl_2$ was added, to give results as mg Ca/g sulfonate.

Blended Alkylaromatic Sulfonates

Processes according to some embodiments further include optional blending so as to obtain a blended alkylaromatic sulfonate composition. For instance, a linear alkyl benzene (LAB) composition may be blended with a precursor alkyl aromatic composition, followed by sulfonation and neutralization of the blend, and/or a linear alkyl benzene sulfonate (LAS) composition blended with an alkylaromatic sulfonate composition to form the blended alkylaromatic sulfonate composition.

That is, processes according to some embodiments further comprise blending a LAB composition with a precursor alkylaromatic composition (in accordance with any of the previously described alkylaromatic compositions of various embodiments) to form a blended alkylaromatic precursor. The blended alkylaromatic precursor is then sulfonated and neutralized in accordance with the previous descriptions of such processes, to obtain the blended alkylaromatic sulfonate composition. In particular of these embodiments, blending the precursor alkylaromatic composition with a LAB composition advantageously prevents phase separation during sulfonation, such that it is not necessary to remove a light oil phase during sulfonation (as noted above with respect to some embodiments in accordance with FIG. 4). Thus, the resulting blended alkylaromatic sulfonate composition may comprise a fraction of compounds other than sulfonatable aromatics (e.g., 0.1 wt %-50 wt %, preferably 0.1 wt %-30 wt %).

In some embodiments, the pre-sulfonation blend comprises 1 wt %-99 wt % LAB composition and 1 wt %-99 wt % precursor alkylaromatic composition. Preferred blend compositions of some embodiments include precursor alkylaromatic composition within a range from a low of any one of 10, 20, 30, 40 or 50 wt %, to a high of 40, 50, 60, 70, or 80 wt %, provided that the high end of the range is greater than the low end. For instance, preferred ranges include, for example, 10-30 wt %, 20-60 wt %, 30-50 wt %, 30-60 wt %, and 40-70 wt % precursor alkylaromatic composition, the wt % based on the total mass of the blended alkylaromatic precursor. The balance of the blended precursor composition comprises the LAB composition. The precursor alkylaromatic composition may be constituted as per any of the previously described alkylaromatic compositions (e.g., as noted previously, comprising sulfonatable aromatics, and particularly 1R, 1.5R, and/or 2+R alkylaromatic compounds, within the range from a low of 35, 40, 45, 50, 55, or 60 wt % to a high of 62, 65, 75, or 80 wt %, such wt %s based on the mass of precursor alkylaromatic composition in the blend).

Advantageously, any conventional LAB composition, such as commercially available A225, may be used. LAB compositions according to some embodiments comprise at least 85 wt %, preferably at least 90 wt %, of various isomers of alkylbenzenes having unbranched alkyl chain length from 8 to 20, preferably from 10 to 16, carbon atoms, with the phenyl moiety located on the 2-10, preferably the 2-5, carbon of the alkyl chain. Thus, LAB compositions comprise at least 85 wt %, preferably at least 90 wt %, more preferably at least 95 wt % (such as at least 98 wt %), of isomers of compounds in accordance with Formula (X) below:

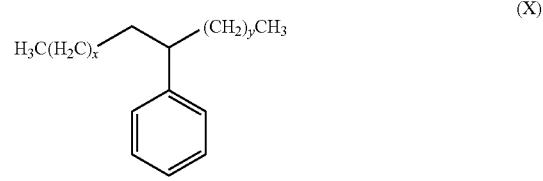

where 6<x+y<18 (preferably where 8<x+y<14), and x and y are each at least 1.

Conveniently, LAB compositions may be obtained from conventional processes for alkylating, benzene to form LABs, which is well known in the art.

Similarly, processes according to some embodiments also or instead may further comprise blending a LAS composition with an alkylaromatic sulfonate composition (or blending a neutralized LAS composition with a neutralized alkylaromatic sulfonate composition) so as to obtain the blended alkylaromatic sulfonate composition.

Suitable LAS compositions may also vary widely in composition. Preferably, suitable LAS compositions are the corresponding sulfonates of such LAB compositions. That is, suitable LAS compositions comprise at least 85 wt %, preferably at least 90 wt %, more preferably at least 95 wt % (such as at least 98 wt %) of isomers of compounds in accordance with Formula (XI) below:

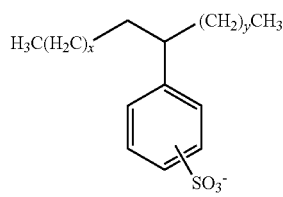

(XI)

where x and y are as discussed above with respect to formula (X). It will be understood that, as with other sulfonate compounds described herein, the LAS compounds in accordance with Formula (XI) are anionic, and therefore may exist in their anionic form or in a salt form (e.g., with ionic bonding to a cationic species, such as $Na^+$, $K^+$, or the like). Therefore, a LAS compound may be characterized as a compound comprising isomers in accordance with Formula (XI), and/or salts thereof.

Processes according to yet further embodiments may include both forms of blending just described, i.e., such processes may include (i) blending LAB compositions with a precursor alkylaromatic composition, (ii) sulfonating the blend, then (iii) further blending with a LAS composition to form the blended alkylaromatic sulfonate composition.

Blended alkylaromatic sulfonate compositions according to various embodiments may comprise 1-99 wt % of a LAS composition and 1-99 wt % of the alkylaromatic sulfonate composition comprising 1R, 1.5R, and/or 2+R alkylaromatic sulfonates, which may be in accordance with any of the foregoing embodiments described with respect to such alkylaromatic sulfonates. Preferred amounts of alkylaromatic sulfonate composition in the blended alkylaromatic sulfonate compositions include a range from a low of any one of 10, 20, 30, or 40 wt %, to a high of 30, 40, 50, 60, or 70 wt %, provided that the high end of the range is greater than the low end. Particular examples include 20-60 wt %, such as 30-50 wt % or 30-60 wt %, alkylaromatic sulfonate composition in the blended alkylaromatic sulfonate compositions.

Blended alkylaromatic sulfonate compositions of some embodiments may exhibit any one or more of the following properties:

Surfactant activity within the range from 25 to 95%, preferably 30 to 80%, 30 to 70%, or 40 to 60%, with ranges from any of the foregoing low ends to any of the foregoing high ends also contemplated in some embodiments.

Critical micelle concentration (CMC) within the range from 0.01-0.1 wt %, such as 0.01-0.05 wt %.

Draves wetting within the range from 5 to 25, preferably 5 to 20, more preferably 5 to 15 sec as determined at 21° C. for 0.1 wt % solution of the blended alkylaromatic sulfonate in water.

Ross-Miles Foam height within the range from 5 to 40 mm, preferably 10 to 35 mm (initial); and/or 5 to 40 mm, preferably 10 to 35 mm (after 5 min), as determined at 21° C. for 0.1 wt % solution of the blended alkylaromatic sulfonate in water.

Interfacial tension (IFT) of a 0.10 wt % solution in distilled water within the range from 1.5 to 3.0, preferably 1.5 to 2.5 mN/m in mineral oil and distilled water interface.

Calcium tolerance within the range from 10 to 30 mg Ca/g blended alkylaromatic sulfonate, such as from 15 to 25 mg Ca/g.

Omitting Hydrocarbon Mixture Treatment

In some embodiments, the previously-described hydrocarbon treatments may be omitted. In this instance, the untreated hydrocarbon mixture may be used in the above-described methods in place of the precursor alkylaromatic composition—that is, the untreated hydrocarbon mixture of such embodiments may be blended with LAB and sulfonated as described above with respect to blending the precursor alkylaromatic composition, or it may be sulfonated without blending, using sulfonation techniques in accordance with the above-described sulfonation techniques.

Such embodiments may be particularly useful in combination with embodiments including one or more blending steps. That is, where an untreated hydrocarbon mixture is to be utilized, such mixture is preferably blended with a LAB composition (in accordance with any of the above-described LAB compositions) and sulfonated. The sulfonated composition is optionally further blended with a LAS composition according to any of the above-described LAS compositions. Alternatively, the untreated hydrocarbon mixture of other embodiments is sulfonated without blending, and the sulfonated product blended with a LAS composition. The cost savings of omitting treatment may be quite advantageous, and the detriment to surfactant performance from the presence of compounds other than sulfonatable aromatics may be advantageously minimized through any of the just-described blending. In embodiments in which a hydrocarbon mixture comprises substantially only 1R alkylaromatics, 1.5R alkylaromatics, or 2+R alkylaromatics (in accordance with embodiments previously described), blending one or more such hydrocarbon mixtures with a LAB composition (or sulfonating and blending with a LAS composition) is particularly advantageous, since treating such hydrocarbon mixtures may not be necessary to maintain acceptable or even superior surfactant performance.

Furthermore, in such embodiments, the hydrocarbon mixture may be obtained from any source—it need not be a refinery cut, and could indeed be obtained as pure hydrocarbon of a desired composition (e.g., purchased or formed through any means of synthesis such as alkylation of a base benzene, naphthalene, or the like). The ordinarily skilled artisan will readily recognize any of the numerous ways in which a given hydrocarbon mixture (e.g., one comprising alkylated naphthalenes and/or di-alkyl benzenes, among others) may be obtained.

For instance, in some particular embodiments, a hydrocarbon mixture comprising at least 80, preferably at least 90, more preferably at least 95 wt % of di-alkylaromatic benzenes in accordance with any one of Formulas (III), (IV), or (V) is blended with a LAB composition and sulfonated to obtain a blended alkylaromatic sulfonate composition. Alternatively, such hydrocarbon mixture comprising the di-alkylaromatic benzene can be subjected to sulfonation, and the sulfonated product blended with a LAS composition to obtain the blended alkylaromatic sulfonate composition. Preferably, the pre-sulfonated blend (i.e., the blended alkylaromatic precursor comprising such hydrocarbon mixture and the LAB composition) comprises from 2 to 60 wt %, preferably 2 to 40 wt %, more preferably from 2 to 25 or even 2 to 20 wt %, of the di-alkylaromatic benzenes; and from 40 to 90 wt %, preferably 60 to 98 wt %, more preferably from 75 to 98 wt % or even 80 to 98 wt % of the LAB composition. Likewise, the corresponding alkylaromatic sulfonate composition may comprise from 2 to 60 wt %, preferably 2 to 40 wt %, more preferably from 2 to 25 wt %, or even 2 to 20 wt %, of the di-alkylaromatic sulfonates; and from 40 to 98 wt %, preferably 60 to 98 wt %, more preferably from 75 to 98 wt %, or even 80 to 98 wt %, of the sulfonated LAB composition (e.g., a LAS composition corresponding to the LAB composition).

As another example, in yet other embodiments, a hydrocarbon mixture comprising at least 80, preferably at least 90, more preferably at least 95 wt % of one or more alkylated naphthalenes is blended with a LAB composition and sulfonated, or sulfonated and then blended with a LAS composition, to form a blended alkylaromatic sulfonate composition. Preferably, the alkylated naphthalenes are mono, di, and/or tri-alkylated. In some embodiments, each naphthalene is in accordance with Formula (VII) (i.e., the hydrocarbon mixture of such embodiments comprises isomers of alkylated naphthalenes each having structure in accordance with Formula (VII)). In such embodiments, the pre-sulfonation blend (i.e., the blended alkylaromatic precursor formed by blending such hydrocarbon mixtures with LAB compositions) comprises from 2 to 60 wt %, preferably 2 to 40 wt %, more preferably from 2 to 25 wt %, or even 2 to 20 wt %, of the alkylated naphthalenes; and from 40 to 98 wt %, preferably 60 to 98 wt %, more preferably from 75 to 98 wt %, or even 80 to 98 wt % of the LAB composition. Likewise, the blended alkylaromatic sulfonate composition preferably comprises from 2 to 60 wt %, preferably 2 to 40 wt %, more preferably from 2 to 25 wt %, or even 2 to 20 wt %, of the corresponding sulfonated alkyl-naphthalenes; and from 40 to 98 wt %, preferably 60 to 98 wt %, more preferably from 75 to 98 wt %, or even 80 to 98 wt %, of the sulfonated LAB composition (e.g., a LAS composition corresponding to the LAB composition).

In yet further embodiments, the hydrocarbon mixture may comprise di-alkyl benzenes (preferably having structures according to any one or more of Formulas (III)-(V)) and alkylated naphthalenes (preferably mono-, di-, or tri-alkylated naphthalenes, more preferably having structure according to formula (VII)). The hydrocarbon mixture is blended with a LAB composition and sulfonated, and/or sulfonated and blended with a LAS composition, to form the blended alkylaromatic sulfonate. The pre-sulfonated blend comprises 2 to 40 wt %, preferably 2 to 25 wt %, or even 2 to 20 wt %, of each of the di-alkyl benzenes and the alkylated naphthalenes, with the balance formed by the LAB composition. The post-sulfonated blend (i.e., the blended alkylaromatic sulfonate) likewise preferably comprises 2 to 40 wt %, more preferably 2 to 25 or 2 to 20 wt %, of each of the corresponding di-alkyl benzene sulfonates and the corresponding alkyl naphthalene sulfonates, with the balance formed by the LAS composition.

Such hydrocarbon mixtures (e.g., comprising di-alkyl benzenes and/or alkylated naphthalenes) may be obtained by any means, with no treatment necessary. For instance, alkylation or other synthetic processes may be used to form such compositions.

The blended alkylaromatic sulfonate compositions formed according to such embodiments may advantageously exhibit very low CMC, such as CMC within the range from 0.001 to 0.01 wt %. Alternatively, such blended alkylaromatic sulfonate compositions may exhibit CMC that is at most 1/10 of the CMC of the LAS composition (i.e., the sulfonated LAB composition) in the absence of the sulfonated hydrocarbon mixture.

Such blended alkylaromatic sulfonate compositions may additionally have IFT, Ca tolerance, and Draves Wetting that are each no more than 10% different from the IFT, Ca tolerance, and Draves Wetting of the LAS composition in the absence of the sulfonated hydrocarbon mixture. For instance, where N is the Ca tolerance of the LAS composition, the blended alkylaromatic sulfonate may have Ca tolerance of at least 0.9N and at most 1.1N (and likewise for IFT and Draves Wetting).

EXAMPLES

Example 1: Effects of Extractions

A distillate feed was hydrotreated to reduce level of heteroatoms to 52 ppm Sulfur and 1 ppm Nitrogen, then cut to a boiling range of 260° C.-340° C. and extract with NMP (66% treat rate, 0.5 wt % $H_2O$ in solvent, 25° C.) to remove 77 wt % of 2-ring (and greater) aromatics in the feed. The extracted hydrocarbon was recovered as Sample 1-1, and a portion of Sample 1-1 was retained for composition analysis, reported in Table X below.

The remaining portion of Sample 1 was extracted at a more severe condition with NMP (225% treat rate, 0.5 wt % $H_2O$ in solvent, 25° C.) to concentrate 1 ring aromatics the extract and generate Sample 1-2. Sample 1-2 was extracted again with NMP (175% treat rate, 0.5 wt % $H_2O$ in solvent, 25° C.) to further concentrate the aromatics in the extract and generate Sample 1-3.

An additional sample (Sample 1-4) was obtained as follows: Another portion of the distillate feed was hydrotreated to reduce the level of heteroatoms to 52 ppm Sulfur and 1 ppm Nitrogen, cut to a boiling range of 260° C.-380° C. (a higher maximum boiling range as compared to Samples 1-3). This sample was then subjected to similar extractions as with Sample 1-3: specifically, it was extracted with NMP (66% treat rate, 0.5 wt % $H_2O$ in solvent, 25° C.) to remove 77% of 2-ring aromatics in the feed, then extracted with NMP at a more severe condition (225% treat rate, 0.5 wt % $H_2O$ in solvent, 25° C.) to concentrate the 1 ring aromatics in the extract, and then extracted again with NMP (175% treat rate, 0.5 wt % $H_2O$ in solvent, 25° C.) to further concentrate the aromatic in the extract and generate Sample 1-4.

A further sample (Sample 1-5) was obtained as follows: Another portion of the distillate feed was hydrotreated to reduce the level of heteroatoms to 52 ppm Sulfur and 1 ppm Nitrogen, cut to a boiling range of 170° C.-260° C. (lower than previous samples), and then subjected to the same three NMP extractions as was Sample 1-4, in the same order.

A final sample (Sample 1-6) was obtained as follows: Another portion of the distillate feed was hydrotreated to reduce the level of heteroatoms to 52 ppm Sulfur and 1 ppm Nitrogen, cut to a boiling range of 170° C.-380° C. (broader than the previous samples), and then subjected to the same 3 extractions, in the same order, as Samples 1-4 and 1-5 were subjected to.

The distribution of saturates, 1R, 1.5R, and 2+R alkylaromatic compounds in all 6 of these samples before sulfonation, measured by 2D-GC, is shown in Table 1.

TABLE 1

Compositions of hydrocarbon streams following extractions

| Sample Generated | Carbon # | No. of Severe EXT | SATS, wt % | 1R, wt % | 1.5R, wt % | 2 + R, wt % |
|---|---|---|---|---|---|---|
| 1-1 | C16-C21 | 0 | 78 | 12 | 8 | 2 |
| 1-2 | C16-C21 | 1 | 46 | 23 | 23 | 8 |
| 1-3 | C16-C21 | 2 | 38 | 23 | 26 | 13 |
| 1-4 | C16-C26 | 2 | 29 | 21 | 27 | 23 |
| 1-5 | C10-C17 | 2 | 44 | 23 | 25 | 8 |
| 1-6 | C10-C26 | 2 | 38 | 22 | 25 | 16 |

Samples 1-1 through 1-3 were further sulfonated and the resulting alkylaromatic sulfonate compositions were tested for Ca tolerance, wetting, foaming, IFT, and CMC. Results are reported in Table 2, along with a comparator LAS composition (A225, available from Huntsman)

TABLE 2

Surfactant properties of Example 1 sulfonates

| | ml 1.0% CaCl$_2$ to Haze No 50 | CMC, % | Draves Cotton Wetting @ 21°, sec, 0.1 wt %, seconds | Ross-Miles Foam @ 21° C., mm, 0.1 wt % | | IFT, mN/m, mineral oil/deionized water | |
|---|---|---|---|---|---|---|---|
| | | | | Initial, mm | 5 min, mm | 0.1% surfactant | 0.5% surfactant |
| Desired | High | Low | Low | Low | Low | Low | Low |
| LAS | 0.31 | 0.01-0.05 | 5.2 | 124 | 119 | 1.60 | 3.06 |
| 1-1 | 0.98 | 0.1-0.5 | >500 | 71 | 52 | 9.44 | 5.96 |
| 1-2 | 1.05 | 0.5-1.0 | 203 | 15 | 13 | 6.63 | 4.01 |
| 1-3 | 0.91 | 0.5-1.0 | >500 | 36 | 23 | 8.34 | 5.46 |

Due to their low foaming and good hardness tolerance, Samples 1-1 through 1-3 are suitable for use as hydrotropes in liquid laundry detergent formulation, e.g., added as 7-15 wt %, such as 11-12 wt % or even 10 wt %, in the total detergent weight mixture or as emulsion breaker (de-emulsifier). Additionally, the low foaming can make these samples good additives in several house hold and industry detergent to decrease foaming when it is not desired. Furthermore, the superior Ca tolerance demonstrated by the ml of CaCl$_2$ required to reach Haze No. 50 for Samples 1-1 through 1-3 indicates the potential for these compositions to be advantageously employed in enhanced oil recovery operations.

Example 2: Sulfonation of Variously Extracted Precursor Alkylaromatic Compositions Three sample precursor alkylaromatic compositions (2-1, 2-2, and 2-3) were obtained through a different number of severe extractions as shown below in Table 3, and analyzed for wt % of sulfonatable aromatics by 2D-GC. The results (and number of severe extractions) are shown below, as compared to a commercial LAB 11 composition (Sample 2-C, which was A225, a 2-dodecylbenzene with 98 wt % purity available from Huntsman) The first severe extraction (# Severe Extractions referenced in Table X+2~, applicable to Samples 2-1 and 2-2) was with NMP (225% treat rate, 0.5 wt % H$_2$O in solvent, 25° C.); the second severe extraction (applicable to Sample 2-1) was also with NMP (175% treat rate, 0.5 wt % H$_2$O in solvent, 25° C.).

TABLE 3

Pre-sulfonation material characterization

| Samples | # Severe Extractions | Sulfonatable compound wt % | Carbon # |
|---|---|---|---|
| 2-C | NA | 98 | C14-C22 |
| 2-1 | 2 | 69 | C16-C21 |
| 2-2 | 1 | 57 | C16-C21 |
| 2-3 | 0 | 29 | C16-C21 |

The A225 was sulfonated in accordance with the following procedure:
1. Added the alkylate to the glass reactor and started stirring.
2. The stirred alkylate was cooled in ice-water to 10° C.-25° C. during the drop wise addition of fuming sulfuric acid.
3. Heated to 50° C. after finishing addition of the fuming sulfuric acid.
4. Held at 50° C. for 3.5 hours.

The sulfonation mixture was then subjected to the following neutralization:

5. The sulfonation mixture was transferred to a dropping funnel and added dropwise to a stirred and ice-cooled solution of diluted NaOH such that the temperature of the mixture does not exceed 40° C. The total weight of water and NaOH was 2010 g which is equivalent to 12.2% NaOH.
6. The precipitated white slurry is transferred into two 1-liter separatory funnels and the lower aqueous phase withdrawn periodically.
7. A total of 1046 g of lower aqueous slurry (sulfonated Sample 2-C) was retained.

The resulting slurry was then purified as follows:
8. The slurry was poured into a 4-liter beaker with 460 g of deionized water added.
9. The slurry was stirred for 15 minutes and vacuum-filtered through a 2.5 micron filter paper. The resulting gelatinous paste was transferred into two heavyweight steel pans for drying in a 75° C. oven to constant weight which required 3.5 days at this temperature.
10. This yielded 331.9 g of sulfonated Sample 2-C.

Samples 2-1, 2-2, and 2-3 were each independently sulfonated according to the following procedure:
1. Added the sample to the glass reactor and started stirring.
2. The stirred alkylate was cooled in ice-water to 10° C.-25° C. during dropwise addition of fuming sulfuric acid.
3. The mixture was heated to 50°-53° C. for 3.5 hours.

4. The dark reaction mixture was cooled to room temp and poured into a separatory funnel.
5. The upper phase was separated to yield unsulfonatable oil (reported for each sample in Table 4a below).

Samples 2-1, 2-2, and 2-3 were then each independently neutralized by dropwise addition of aqueous NaOH that was diluted with water to 300 g to yield an aqueous liquid containing a crystalline mass, for each sample.

Each sample was then purified as follows:
6. Each crystalline mass-containing aqueous liquid was filtered to yield a wet solid and a filtrate. Titration of the filtrate for active was carried out to determine the activity of the sample.
7. This aqueous solution, was poured into iron pans and concentrated to dryness in a 75° C. oven.
8. The resulting solids were extracted with hot IPA and suction filtered.
9. The IPA filtrate was concentrated on a rotary evaporated vacuum to dryness. This yielded the amount of sulfonated product reported in Table 4a below for each Sample.

Table 4a shows the charging materials, sulfonated product, and activity for Samples 2-C, 2-1, 2-2, and 2-3. Table 4b below shows the conversion of total aromatics, and the conversion of each of the 1R, 1.5R, and 2+R aromatics (i.e., wt % of each type of aromatic sulfonated during the sulfonation reaction, as determined from 2D-GC).

TABLE 4a

Sulfonation parameters and products for Example 2

| Sample | mass (g) | Arom. Rings (mmol) | $H_2SO_4$ + $SO_3$ (g) | Oil Phase (g) withdrawn during sulfonation | Arom. Rings in sulfonate (mmol) | Sulfonated product (g) | Activity (%) |
|---|---|---|---|---|---|---|---|
| 2-C | 246 | 1000 | 332.7 | NA | NA | 331.9 | 90.3 |
| 2-1 | 124.1 | 313 | 100.0 | 60 | 183.5 | 14.6 | 68.4 |
| 2-2 | 137.4 | 247 | 96 | 79.2 | 180.4 | 22.8 | 76.2 |
| 2-3 | 247.3 | 166 | 73.5 | 217.1 | 54.6 | 4.5 | 65.8 |

TABLE 4B

Aromatic Conversions in Sulfonation of Example 2

| Sample | Conversion of Total Aromatics | Conversion 1R | Conversion 1.5R | Conversion 2 + R |
|---|---|---|---|---|
| 2-1 | 80.50 wt % | 64.26 wt % | 86.98 wt % | 96.28 wt % |
| 2-2 | 79.72 wt % | 67.42 wt % | 88.92 wt % | 92.79 wt % |
| 2-3 | 56.07 wt % | 34.11 wt % | 67.05 wt % | 100.00 wt % |

The mmol of aromatic rings in the sulfonate was calculated by combining data from 2D-GC, carbon weight percent, and C-NMR. First, the moles of total aromatic carbon per kg of sample was calculated from the wt % C of the sample and its fraction of aromatic carbon, as obtained by C-NMR:

$$n(C_{AROMATIC})/\text{kg sample} = \frac{\text{wt \% C}/100 * 1000 \text{ g}}{12 \text{ g/mol}} * \frac{\text{\% C Aromatic}}{100}.$$

Next, the moles of aromatic rings per kg of sample were calculated by multiplying the above-derived moles aromatic carbon by the 2D-GC obtained fraction of 1, 2, and 3-ring aromatics in the sample, divided by the number of carbons per respective aromatic rings class and multiplied by the number of rings in the respective class of aromatic as shown below (where "3RA" means 3-ring aromatic, "2RA" means 2-ring aromatics, and "1RA" means 1-ring aromatics):

Moles of aromatic rings/kg sample=(%3RA/100*$n(C_{AROMATIC})$/14*3+%2RA/100*$n(C_{AROMATIC})$/10*2+%1RA/100*$n(C_{AROMATIC})$/6).

CMC was determined at 22° C. in distilled water for each sulfonated sample. FIGS. 5, 7, 9, and 11 each show a graph of surface tension (mN/m) vs. sulfonated Sample concentration in water (wt %), which was used to determine CMC for each sulfonated Sample 2-C, 2-1, 2-2, and 2-3, respectively. Calcium tolerance was determined for each sulfonated sample in distilled water (0.10 wt % solution) by titrating 50 g of a 0.1% sample solution (0.05 g) with 1.00 wt % calcium chloride (3.64 mg Ca/ml) to a haze value of 50. FIGS. 6, 8, 10, and 12 are each a graph of ml 1% $CaCl_2$ vs. Haze No.; the ml value of the 1% $CaCl_2$ solution at 50 Haze was used to determine the calcium tolerance, based upon the value of 3.64 mg Ca/ml to convert from ml of 1% $CaCl_2$ solution to g Ca required to bring the 0.05 g sample to Haze value 50.

Draves wetting was also determined for a 0.10 wt % solution of each sulfonated sample in distilled water at 22° C.; Ross-Miles Foam height was determined at 22° C. for each sulfonated sample; and IFT was run against mineral oil at 22° C. in distilled water and recorded at 0.1 wt % and 0.5 wt % concentrations of each sulfonated sample in water.

The results of each test for each sulfonated sample are summarized in Table 5 below. As shown in Table 5, while the sulfonated products obtained using only severe NMP extractions may have inferior cleaning detergent properties as compared to the comparator commercial LAS, they have far superior calcium tolerance, indicating that they could be particularly useful in enhanced oil recovery operations.

TABLE 5

Performance testing for Example 2 sulfonated samples

| Sample | CMC, % | Draves Wetting(s) | Ross-Miles Foaming, initial, mm | Ross-Miles Foaming, 5 min, mm | IFT, 0.1% conc., mN/m | IFT, 0.5% conc., mN/m | Calcium Tolerance, mCa/g |
|---|---|---|---|---|---|---|---|
| 2-C | 0.01-0.05 | 5.2 | 124 | 119 | 1.60 | 3.06 | 22.6 |
| 2-1 | 0.01-0.05 | >500 | 71 | 52 | 9.44 | 5.96 | 71.3 |
| 2-2 | 0.5-1.0 | 203 | 15 | 13 | 6.63 | 4.01 | 76.4 |
| 2-3 | 0.5-1.0 | >500 | 36 | 23 | 8.34 | 5.46 | 66.2 |

Example 3: Blended Alkylaromatic Sulfonate Compositions

Portions of the un-sulfonated Samples 2-1, 2-2, and 2-3 were each sulfonated to obtain sulfonated samples corresponding to each of Samples 2-1, 2-2, and 2-3, and differing amounts of the unsulfonatable phase resulting from the sulfonation reaction were removed from each sulfonated sample. The sulfonated samples were then each blended with a separately sulfonated A225 alkylate (2-dodecylbenzene with 98 wt % purity, from Huntsman), thereby obtaining blended alkylaromatic sulfonates. Table 6 below summarizes the blended alkylaromatic sulfonate samples thusly created (including amounts of unsulfonatable oil remaining in each blend, and relative amounts of sulfonated product and sulfonated A225 alkylate used in each blend). In Table 6, the portion of each blend corresponding to the precursor alkylaromatic compositions described above in connection with various embodiments is the sum of both columns "Sulfonated product" and "unsulfonatable oil" (corresponding respectively to the sulfonates of the sulfonatable aromatics and compounds other than sulfonatable aromatics (e.g., saturates) of the precursor alkylaromatic compositions).

TABLE 6

Example 3 Sample blends for performance testing

| Sample | Derived from Ex. 2 Sample | Sulfonated product (wt %) | Unsulfonatable Oil (wt %) | A225 alkylate (wt %) |
|---|---|---|---|---|
| 3-1 | 2-1 | 10 | 4 | 86 |
| 3-2 | 2-1 | 30 | 12 | 58 |
| 3-3 | 2-1 | 40 | 16 | 44 |
| 3-4 | 2-2 | 10 | 6 | 84 |
| 3-5 | 2-2 | 20 | 12 | 68 |
| 3-6 | 2-2 | 30 | 18 | 52 |
| 3-7 | 2-3 | 10 | 8 | 82 |
| 3-8 | 2-3 | 20 | 16 | 64 |
| 3-9 | 2-3 | 30 | 24 | 46 |

Draves Wetting testing was carried out on all the samples. In addition, Ross-Miles Foam, IFT, CMC, and Ca tolerance testing were carried out on Samples 3-2 and 3-5. The results are reported in Table 7 below, with test results of the A225 LAS composition reported as Sample 3-C for comparison. Draves wetting was determined at 21° C. for a 0.10 wt % solution of the sample in distilled water. Ross-Miles Foam height was run at 21° C. in distilled water for a 0.10 wt % solution in water, with data recorded initially and after 5 minutes. Interfacial tension (IFT) was run against mineral oil at 21° C. in distilled water for 0.1 wt % sample in water, and Ca tolerance determined in the same manner as described with respect to Example 2.

TABLE 7

Performance Testing of Example 3 Sample Blends

| Sample | Draves Wetting @ 21° C. 0.1 wt %, Second | Ross-Miles Foam @ 21° C., mm, 0.1 wt % | | IFT, mN/m, mineral oil/DIW 0.1% surfactant | CMC Wt % | Ca tolerance Mg Ca/g |
|---|---|---|---|---|---|---|
| | | Initial, mm | 5 mm, mm | | | |
| 3-C | 5.2 | 124 | 119 | 1.60 | 0.01-0.05 | 22.6 |
| 3-1 | 16 | — | — | — | — | — |
| 3-2 | 11 | 34 | 30 | 2.49 | 0.01-0.1 | 23 |
| 3-3 | 17 | — | — | — | — | — |
| 3-4 | 8 | — | — | — | — | — |
| 3-5 | 8 | 10 | 10 | 1.66 | 0.01-0.1 | 17 |
| 3-6 | 18 | — | — | — | — | — |
| 3-7 | 11 | — | — | — | — | — |
| 3-8 | 14 | — | — | — | — | — |
| 3-9 | 18 | — | — | — | — | — |

The blending tests show some very interesting results. While the alkylaromatic sulfonate compositions according to Example 2 exhibited far superior Ca tolerance and Ross-Miles foaming to conventional commercial LAS, but inferior cleaning detergent properties such as Draves Wetting, IFT, and CMC, the blends of Example 3 indicate that the advantageously low foaming may be maintained by blending alkylaromatic sulfonates with conventional LAS compositions. At the same time, however, significant gains are made in the detergent properties (Draves wetting, IFT, CMC) in the blends of Example 3, as compared to the properties of alkylaromatic sulfonates of Example 2. However, the Ca tolerance advantage of the non-blended compositions of Example 2 is lost when blended with conventional LAS composition.

In sum, the data suggests that alkylaromatic sulfonate compositions according to various embodiments provide substantial flexibility in their employment; they may be blended to form detergent compositions with excellent surfactant properties for detergent and similar cleaning applications, which advantageously also exhibit very low foaming. Or, they may remain un-blended and be utilized in applications where high Ca tolerance is demanded, such as enhanced oil recovery, or as hydrotropes/emulsion breakers (de-emulsifiers).

Example 4: Blending Specific Compounds with LAS Compositions

Figure 13:
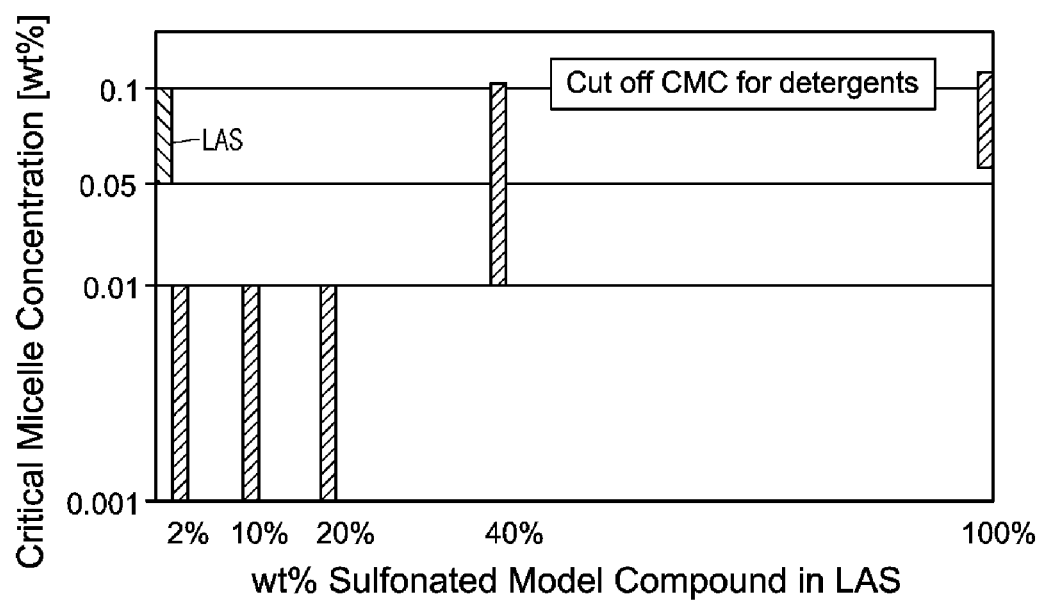
FIG. 13 is a graph showing CMC ranges measured for various blend compositions in connection with Example 4.

A hydrocarbon mixture comprising high wt % of an alkylated naphthalene was blended with LAS compositions to determine whether such blend partners improve surfactant properties with LAS compositions. In particular, 2, 10, 20, and 40 wt % of sulfonated 6,7-dimethyl-1-(4-methylpentyl)-Naphthalene was blended with A225 (2-dodecylbenzene, 98 wt % purity, available from Huntsman) FIG. 13 shows the CMC range measured for each blend. Surprisingly, blends as low as 2 wt % and up to 20 wt % of the alkylated naphthalene in the sulfonated A225 composition yielded a significantly lower CMC value (0.001-0.01 wt %) as compared to the conventional LAS (sulfonated A225) composition on its own (CMC of 0.05-0.1 wt %). At the same time, the Draves Wetting and Ca tolerance of the conventional LAS were not significantly changed. In particular, regarding Ca tolerance, the variation of all blends from the pure LAS lies within the experimental error. In some cases it even increases. The worst case data point is the decrease of Ca-tolerance of 4%, which is still quite acceptable. The worst case of wetting is observed in the 40 wt % case (40 wt % of the sulfonated 6,7-dimethyl-1-(4-methylpentyl)-naphthalene in the blend), in which case wetting is increased from 5 (pure LAS) to 9, which is still considered good wetting for detergents.

The same trends are observed when blending di-alkylated benzenes with LAS. For instance, Table 8 shows Draves Wetting, CMC, Ca Tolerance, Ross-Miles Foam @ 21° C. (initial and 5-min, in mm) for blends of p-dodecyl toluene (Sample 4-1) with A225; and blends of p-dioctylbenzene (Sample 4-2) with A225. Both Sample 4-1 and 4-2 are examples of di-alkylated benzenes according to some embodiments. Table 8 also includes the performance data for 6,7-dimethyl-1-(4-methylpentyl)-naphthalene (labeled as Sample 4-3), discussed above. The same performance test values for the commercial A225 LAS are reproduced from Table 7 to Table 8, for comparison.

TABLE 8

LAS Blend Study Performance Testing

| Blend | Draves Wetting @ 21° C. 0.1 wt %, Second | Ross-Miles Foam @ 21° C., mm, 0.1 wt % | | CMC Wt % | Ca tolerance Mg Ca/g sulfonate |
|---|---|---|---|---|---|
| | | Initial, mm | 5 min, mm | | |
| Detergent Criteria | <20 | — | — | <0.1 | ~22.6 |
| 100% A225 | 5.2 | 124 | 119 | 0.01-0.05 | 22.6 |
| 100 wt % 4-1 | 2.1 | 135 | 127 | 0.01-0.05 | 158.7 |
| 40/60 wt % (4-1/A225) | 6.0 | 160 | 150 | 0.001-0.01 | 20.3 |
| 10/90 wt % (4-1/A225) | 7.9 | 160 | 150 | 0.001-0.01 | 26.0 |
| 100% 4-2 | 7.5 | 108 | 89 | 0.01-0.05 | 0 |
| 40/60 wt % (4-2/A225) | 6.1 | 150 | 135 | 0.001-0.01 | 22.7 |
| 10/90 wt % (4-2/A225) | 6.4 | 160 | 148 | 0.001-0.01 | 23.7 |
| 100% 4-3 | >500 | 15 | 10 | 0.06-0.13 | 131.04 |
| 40/60 wt % (4-3/A225) | 9.0 | 130 | 110 | 0.01-0.1 | 21.6 |
| 20/80 wt % (4-3/A225) | 7.0 | 130 | 120 | 0.001-0.01 | 31.4 |
| 10/90 wt % (4-3/A225) | 7.0 | 140 | 120 | 0.001-0.01 | 22.2 |
| 2/98 wt % (4-3/A225) | 6.0 | 130 | 120 | 0.001-0.01 | 29.4 |

In all cases, independent of substitution position and length (within the bounds of total carbon numbers in the various embodiments described herein), detergent criteria are met when up to 40 wt % of the blend partner compositions are added to the conventional sulfonated A225.

This suggests that blending conventional LAS compositions with hydrocarbon mixtures comprising high wt % (e.g., at least 90, 95, 98, 99, or even 100 wt %) of a particular compound or class of compounds (e.g., alkylated naphthalenes) may provide substantial advantages to surfactant properties of the blended alkylaromatic sulfonate.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention. The contents of all references cited herein are incorporated by reference in their entirety.

The invention claimed is:
1. A process comprising:
(a) blending a hydrocarbon mixture comprising one or both of alkylated naphthalenes and di-alkyl benzenes with a linear alkyl benzene (LAB) composition so as to obtain a blended alkylaromatic precursor comprising (i) from 2 to 60 wt % of the alkylated naphthalenes, and/or (ii) from 2 to 60 wt % of the di-alkyl benzenes, provided that total wt % of alkylated naphthalenes and di-alkyl benzenes in the blended alkylaromatic precursor does not exceed 80 wt %;
wherein the LAB composition comprises at least 95 wt % of isomers of one or more compounds each in accordance with Formula (X):

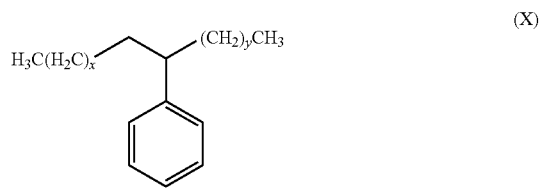

where 6<x+y<18, and x and y are each at least 1; and further wherein the alkylated naphthalenes are selected from the group consisting of mono-alkylated naphthalenes, di-alkylated naphthalenes, tri-alkylated naphthalenes, and combinations thereof, and the di-alkylbenzenes are each in accordance with any one of Formulas (III), (IV), or (V) below:

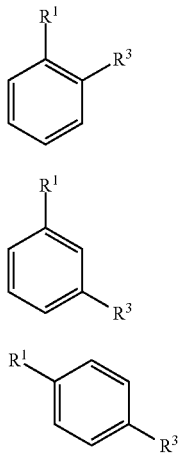

(III)

(IV)

(V)

where, in each of Formulas (III) (V), $R^1$ and $R^3$ are each independently $C_1$-$C_{15}$ alkyl that is either unbranched or, if branched, has pendent chains no longer than 2 carbon atoms; and (b) sulfonating the blended alkylaromatic precursor composition to obtain a blended alkylaromatic sulfonate composition.

2. The process of claim 1, wherein the alkylated naphthalenes each have structure in accordance with Formula (IX)

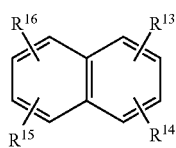

(IX)

where each of $R^{13}$, $R^{14}$, $R^{15}$, and $R^{16}$ is independently selected from H and $C_1$-$C_{15}$ alkyl, provided that the total number of carbon atoms in Formula (IX) does not exceed 30, and furthermore wherein each of $R^{13}$-$R^{15}$ is either unbranched, or has branching such that pendent chains contain no more than 2 carbon atoms.

3. The process of claim 1, wherein the hydrocarbon mixture comprises at least 95 wt % of the alkylated naphthalenes, and the blended alkylaromatic precursor comprises (i) from 2 to 60 wt % of the alkylated naphthalenes, and (ii) from 40 to 98 wt % of the LAB composition.

4. The process of claim 3, wherein the blended alkylaromatic precursor comprises (i) from 2 to 25 wt % of the alkylated naphthalenes, and (ii) from 75 to 98 wt % of the LAB composition.

5. The process of claim 2, wherein each of the alkylated naphthalenes is a tri-alkyl-substituted naphthalene, such that one of $R^{13}$-$R^{15}$ is H.

6. The process of claim 4, wherein $R^{13}$ is H, $R^{14}$ is $C_4$-$C_{12}$ alkyl, and $R^{15}$ and $R^{16}$ are each $C_1$-$C_3$ alkyl.

7. The process of claim 5, wherein each of the alkylated naphthalenes is 6,7-dimethyl-1-(4-methylpentyl)-Naphthalene.

8. The process of claim 1, wherein the hydrocarbon mixture comprises at least 95 wt % of the di-alkylbenzenes, and the blended alkylaromatic precursor comprises (i) from 2 to 60 wt % of the di-alkylbenzenes, and (ii) from 40 to 98 wt % of the LAB composition.

9. The process of claim 8, wherein the blended alkylaromatic precursor comprises (i) from 2 to 20 wt % of the di-alkylbenzenes, and (ii) from 80 to 98 wt % of the LAB composition.

10. The process of claim 1, wherein the blended alkylaromatic sulfonate composition exhibits Critical micelle concentration (CMC) that is at most ⅒ of the CMC of the sulfonated LAB composition in the absence of the sulfonated hydrocarbon mixture.

* * * * *